(12) United States Patent
Tamanoi et al.

(10) Patent No.: US 9,125,821 B2
(45) Date of Patent: Sep. 8, 2015

(54) NANODRUG TARGETING PROTEIN GERANYLGERANYLATION

(71) Applicants: The Regents of the University of California, Oakland, CA (US); NOF CORPORATION, Shibuya-ku, Tokyo (JP)

(72) Inventors: Fuyuhiko Tamanoi, Los Angeles, CA (US); Jie Lu, Los Angeles, CA (US); Kohei Yoshimura, Kawasaki (JP); Ohyun Kwon, Los Angeles, CA (US); Hannah Fiji, Fontana, CA (US); Masaru Watanabe, Yahaba (JP)

(73) Assignees: THE REGENTS OF THE UNIVERSITY OF CALIFORNIA, Oakland, CA (US); NOF CORPORATION, Tokyo (JP)

( * ) Notice: Subject to any disclaimer, the term of this patent is extended or adjusted under 35 U.S.C. 154(b) by 0 days.

(21) Appl. No.: 14/447,176

(22) Filed: Jul. 30, 2014

(65) Prior Publication Data

US 2014/0341979 A1    Nov. 20, 2014

Related U.S. Application Data

(63) Continuation-in-part of application No. 13/614,789, filed on Sep. 13, 2012, now Pat. No. 8,815,935, which is a continuation of application No. 13/056,077, filed as application No. PCT/US2008/009106 on Jul. 28, 2008, now abandoned.

(51) Int. Cl.

| C07D 207/48 | (2006.01) |
| C07D 213/89 | (2006.01) |
| A61K 31/402 | (2006.01) |
| A61K 31/4418 | (2006.01) |
| A61K 9/127 | (2006.01) |
| A61K 31/40 | (2006.01) |
| A61K 45/06 | (2006.01) |
| C07D 207/20 | (2006.01) |
| C07D 211/96 | (2006.01) |
| A61K 31/216 | (2006.01) |

(52) U.S. Cl.
CPC ............ *A61K 9/127* (2013.01); *A61K 31/216* (2013.01); *A61K 31/40* (2013.01); *A61K 31/402* (2013.01); *A61K 31/4418* (2013.01); *A61K 45/06* (2013.01); *C07D 207/20* (2013.01); *C07D 207/48* (2013.01); *C07D 211/96* (2013.01); *C07D 213/89* (2013.01)

(58) Field of Classification Search
None
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 8,093,274 B2 | 1/2012 | Tamanoi et al. |
| 8,445,712 B2 | 5/2013 | Arai et al. |

FOREIGN PATENT DOCUMENTS

| WO | WO-2004015130 A2 | 2/2004 |
| WO | WO-2004110996 A1 | 12/2004 |
| WO | WO-2007111948 A2 | 10/2007 |

OTHER PUBLICATIONS

Carrico, D. et al, (2005) Design, synthesis, and evaluation of potent and selective benzoyleneurea-based inhibitors of protein geranylgeranyltransferase-1, Bioorg. Med Chem. vol. 13, pp. 677-688.
O'Regan, R.M. et al., (2004) Farnesyl transferase inhibitors: the next targeted therapies for breast cancer? Endocr. Relat. Cancer vol. 11, pp. 191-205.
Oualid, F.E. et al., (2005) A Combinatorial Approach toward the Generation of Ambiphilic Peptide-Based Inhibitors of Protein:Geranylgeranyl Transferase-1, J. Comb. Chem. vol. 7, pp. 703-713.
Peterson, Y.K. et al., (2006) A Novel Protein Geranylgeranyltransferase-I Inhibitor with High Potency, Selectivity and Cellular Activity, J. Biol. Chem., Published Mar. 3.
Richter, H. et al., "Polymer Bound 3-Hydroxy-2-methylidenepropionic Acids. A Template for Multiple Core Structure Libraries" J. Org. Chem. 1999, vol. 64, pp. 1362-1365.
Purandare, A. V. et al., "Solid-phase synthesis of 'diverse' heterocycles" Tetrahedron Lett. 2002, vol. 43, pp. 3903-3906.
Huang, X.et al., "Solid-Phase synthesis of 4(1H)-Quinolone and Pyrimidine Derivatives Based on a New Scaffold-Polymer-Bound Cyclic Malonic Acid Ester"J. Org.. Chem. 2002, vol. 67, pp. 6731-6737.
Couladouros E. A.et al., "Generation of Libraries of Pharmacophoric Structures with Increased Complexity and Diversity by Employing Polymorphic Scaffolds". Angew. Chem., Int. Ed. 2002, vol. 41, pp. 3677-3680.
Bertozzi, F. et al., "A Combinatorial Scaffold Approach Based upon a Multicomponent Reaction" Org. Lett. 2003, vol. 5, pp. 1551-1554.
Taylor, S. J. et al., "Synthetic Strategy toward Skeletal Diversity via Solid-Supported, Otherwise Unstable Reactive Intermediates" Angew. Chem., Int. Ed. 2004, vol. 43, pp. 168 1-1685.
Tempest, P.A et al., (1997) Cyclobutenedione derivatives on solid support: Toward multiple core structure libraries. J. Am. Chem. Soc. vol. 119, pp. 7607-7608.
Ding, S. et al., "A Combinatorial Scaffold Approach toward Kinase-Directed Heterocycle Libraries" J. Am. Chem. Soc. 2002, vol. 124, pp. 1594-1596.

(Continued)

*Primary Examiner* — Michael Barker
(74) *Attorney, Agent, or Firm* — Venable, LLP; Keith G. Haddaway; Nancy J. Axelrod

(57) ABSTRACT

The present invention relates, for example, to a liposome, which can be a basic liposome, a transferrin-conjugated liposome, or a pH-sensitive liposome, which encapsulates a compound that specifically inhibits the activity of a protein prenyltransferase, such as a RabGGTase and/or a GGTase I. The liposomes can be used as anti-cancer therapeutics including as part of methods for treating cancer, in assays, and in kits.

25 Claims, 16 Drawing Sheets

(56) References Cited

OTHER PUBLICATIONS

Kwon, O. et al., "Skeletal Diversity via a Branched Pathway: Efficient Synthesis of 29,400 Discrete, Polycyclic Compounds and Their Arraying into Stock Solutions" J. Am. Chem. Soc. 2002, vol. 124, pp. 13402-13404.
Burke, M. D. et al., "Generating Diverse Skeletons of Small Molecules Combinatorially" Science 2003, vol. 302, pp. 613-618.
Clark, E.A. et al., (2000) Genomic analysis of metastasis reveals an essential role for RhoC. Nature vol. 406, pp. 466-467.
Hakem, A. et al., (2005) RhoC is dispensable for embryogenesis and tumor initiation but essential for metastasis. Genes & Develop. vol. 19, pp. 1974-1979.
Lobell, R.B. et al., (2002) Preclinical and clinical pharmacodynamic assessment of L-778,123, a dual inhibitor of farnesyl:protein transferase and geranylgeranyl:protein transferase type-I Mol. Cancer Ther. vol. 1, pp. 747-758.
McGovern, S.L. et al., (2003) A common mechanism underlying promiscuous inhibitors from virtual and high-throughput screening. J. Med. Chem. vol. 45, pp. 1712-1722.
McGovern, S.L. et al., (2003) A specific mechanism of nonspecific inhibition. J. Med. Chem. vol. 46, pp. 4265-4272.
Finegold, A.A. et al., (1991) Protein geranylgeranyltransferase of *Saccharomyces cerevisiae* is specific for Cys-Xaa-Xaa-Leu motif and requires the CDC43 gene product but not the DPRI gene product. Proc. Natl. Acad. Sci. USA vol. 88, pp. 4448-4452.
Furka, A. et al., (1988), in Highlights of Modern Biochemistry, Proceedings of the 14th International Congress of Biochemistry, Prague, Czechoslovakia (VSP, Utrecht, Netherlands), vol. 13, pp. 47.
Furka, A. et al., (1991), Int. J. Pept. Protein Res. vol. 37, pp. 487.
Houghton, R. A. et al., (1991) "Generation and use of synthetic peptide combinatorial libraries for basic research and drug discovery" Nature vol. 354, pp. 84-86.
Lam, K. S. et al., (1991) "A new type of synthetic peptide library for identifying ligand-binding activity" Nature vol. 354, pp. 82-84.
Mukaiyama, T. et al., (1975), "A Convenient Method for the Synthesis of Carboxylic Esters" Chem. Lett. pp. 1045-1048.
Mukaiyama, T. et al., (1976) "Betaine as an Effective Acid Captor: A Convenient Method for the Synthesis of Carboxylic Esters" Chem. Lett. vol. 13-14.
Saigo, K. et al., (1977) "New Method for the Preparation of Carboxylix Esters" Bull. Chem. Soc. Jpn. vol. 50, pp. 1863-1866.
Miyata, O. et al., (1991) "Stereospecific Nucleophilic Addition Reactions to Olefins. Addition of Thiols to αβ-Unsaturated Carboxylic Acid Derivatives" J. Org. Chem. vol. 56, pp. 6556-6564.
Ball, C. P. et al., (1998) "Chameleon Catches in Combinatorial Chemistry: Tebbe Olefination of Polymer Supported Esters and the Synthesis of Amines, Cyclohexanones, Enones, Methyl Ketones and Thiazoles" Chem. Commun. pp. 2019-2020.
Barrett, A. G. M. et al., (2001) "Solid-Phase Synthesis of Isoxazoles Using Vinyl Ethers as Chamelon Catches" Org. Lett. vol. 3, pp. 3165-3168.
Mori, A. et al., (1985) "Resolution of Ketones via Chiral Acetals. Kinetic Approach" J. Org. Chem., vol. 50, pp. 5444-5446.
Lienhard, G. E. et al., (1969) "On the Mechanism of Acid-Catalyzed Enolization of Ketones" J. Am. Chem. Soc. vol. 91, pp. 1146-1153.
Lang, R. W. et al., (1990) "α-Allenic Esters from α-Phosphoranylidene Esters and Acid Chlorides: Ethyl 2,3-Pentadienoate" Org. Synth. Coll. vol. 7, pp. 232-235.
Scholz, D. et al., (1999) "Expedient Synthesis of α-substituted αβ-unsaturated γ-amino acids (dipeptide memetics); Wittig reaction of α-amino aldehydes with a-substituted alkoxycarbonylphosphoranes" Synth. Commun. vol. 29, pp. 1143-1155.
McKay, W. R. et al., (1981) "Removal of toluene-*p*-sulfonyl groups from sulfonamides. Part 4. Synthesis of phenylglyoxal imine monomers" J. Chem. Soc., Perkin Trans. vol. 1, pp. 2435-2442.
Jennings, W. B. et al., (1991) "The titanium tetrachloride induced synthesis of N-phosphinoylimines and N-sulfonylimines directly from aromatic aldehydes". Tetrahedron, vol. 47, pp. 5561-5568.

Love, B. E. et al., (1994) "Preparation of N-Tosylaldimines" Synlett pp. 493-494.
Bilodeau, M. T. et al., (1998) "Solid-Supported Synthesis of Irnidazoles: A strategy for Direct Resin-Attachment to the Imidazole Core," J. Org. Chem. vol. 63, pp. 2800-2801.
Chemla, F. et al., (2000) "An Easy Synthesis of Aliphatic and Aromatic N-Sulfonyl Aldimines," Synthesis, pp. 75-77.
Gerritz, S.W. et al., (2003) "High-Throughput Manual Parallel Synthesis Using SynPhase Crowns and Lanterns" J. Comb. Chem. vol. 5, pp. 110-117.
Feliu, L. et al., (2003) "Spiroimidazolidinone Library Derivatives on SynPhase Lanterns" J. Comb. Chem. vol. 5, pp. 356-361.
Lim, K.H. et al., (2006), Current Biology vol. 16, pp. 2385.
Lim, K.H. et al., (2005), Cancer Cell vol. 7, pp. 533.
Vogt, A.et al., J. Biol. Chem. vol. 272, pp. 27224. (1997).
Mira J-P et al., PNAS vol. 97, pp. 185. (2000).
Pille, J-Y et al., Molecular Therapy vol. 11, pp. 267. (2004).
Hakem A. et al., Genes & Dev. vol. 19, pp. 1974.
Clark, E.A. et al., Nature vol. 406, pp. 532. (2000).
Sebti and Hamilton (2001) Farnesyltransferase and geranylgeranyltransferase I inhibitors as novel agents for cancer and cardiovascular diseases. In "Farnesyltransferase inhibitors in cancer therapy" eds. Sebti and Hamilton, Humana Press, pp. 197-219.
Tamanoi et al. (2001) Protein farnesylation in mammalian cells: effects of farnesyltransferase inhibitors on cancer cells. Cell. Molec. Life Sciences vol. 58, pp. 1636-1649.
Zhao, G.-L. et al., (2005) "Aza-Baylis-Hillman Reactions of N-Tosylated Aldimines with Activated Allenes and Alkynes in the Presence of Various Lewis Base Promoters," J. Org. Chem. vol. 70, pp. 9975-9984.
Wurz, R.P. et al., (2005) "Catalytic Asymmetric Synthesis of Piperidine Derivatives through the [4+2] Annulation of Imines with Allenes," J. Am. Chem. Soc., 2005, vol. 127, pp. 12234-12235.
Zhu, X.-F. et al., (2005) "A highly diastereoselective synthesis of 3-carbethoxy-2,5-disubstituted-3-pyrrolines by phosphine catalysis," Tetrahedron, vol. 61, pp. 6276-6282.
Zhu, X.-F. et al., (2003), An Expedient Phosphine-Catalyzed [4+2] Annulation: Synthesis of Highly Functionalized Tetrahydropyridines, J. Am. Chem. Soc., vol. 125, pp. 4716-4717.
Shi, M. et al., (2002) "Lewis Base Effects in the Baylis-Hillman Reaction of Imines with Methyl Vinyl Ketone," Eur. J. Org. Chem, pp. 696-701.
Xu, Z. et al., (1999), "Phosphine-catalyzed [3+2] cycloaddition reactions of substituted 2-alkynoates or 2,3-allenoates with electron-deficient olefins and imines," Tetrahedron Letters, vol. 40, pp. 549-552.
Vasudevan, A. et al., (1999), "Potent, Highly Selective, and Non-Thiol Inhibitors of Protein Geranylgeranyltransferase-I," J. Med. Chem., vol. 42, pp. 1333-1340.
PCT Application No. US2007/07135, International Search Report dated May 30, 2008.
PCT Application No. US2007/07135, Written Opinion of the International Search Authority dated May 30, 2008.
Yuba, E et al., "The Application of pH-Sensitive Polymer-Lipids to Antigen Delivery for Cancer Immunotherapy", Biomaterials, vol. 34, pp. 5711-5721. (2013).
Ma, S et al., "An Efficient Synthesis of 4-Halo-5-hydroxyfuran-2(5H)-ones via the Sequential Halolactonization and y-Hyrdroxylation of 4-Aryl-2,3-alkadienoic Acids", Journal of Organic Chemistry, vol. 69, pp. 1429-1431. (2004).
Castellano, et al., J.A.C.S., vol. 129, pp. 5843-5845. (2007).
Lu et al., "In vivo Antitumor Effect of a novel Inhibitor of Protein Geranylgeranitransferase-I", Molecular Cancer Therapy, vol. 8, No. 5, pp. 1218-1226. (2009).
Chan et al, Identification adn Characterization of Mechanism of Action of P61-E7, a Novel Phosphine Catalysis-Based Inhibitor of Geranylgeranyltransferase-I, Plos One, vol. 6, Issue 10, pp. 1-13. (2011).
Watanabe et al., "Inhibitors of Protein Geranylgeranyltransferase-I and Rab Geranylgeranyltransferase identified from a Library of Allenoate-derived Compunds", Journal of Biological Chemistry, vol. 23, No. 15, pp. 9571-9579. (2008).
Fang et al., "The EPR Effect: Unique Features of Tumor Blood Vessels For Drug Delivery, Factors Involved, and Limitations and Augmentation of the Effect", Advanced Druge Delivery Reviews, vol. 63, pp. 136-151. (2011).

NANODRUG TARGETING PROTEIN GERANYLGERANYLATION

This application is a continuation-in-part of U.S. application Ser. No. 13/614,789, filed Sep. 13, 2012, which is a continuation of U.S. application Ser. No. 13/056,077, filed Jan. 26, 2011, which is a national stage of International Application No. PCT/US2008/009106, which was filed on Jul. 28, 2008, all of which are incorporated by reference herein in their entireties.

This invention was made with Government support under CA032737, CA041996, GM071779, and GM081282 awarded by the National Institutes of Health. The Government has certain rights in the invention.

BACKGROUND INFORMATION

Protein prenyltransferases, such as protein farnesyltransferase (FTase), RabGGTase (or GGTase-II) and protein geranylgeranyltransferase type I (GGTase-I), catalyze posttranslational modification of proteins, often involving the addition of isoprenoids. For example, protein geranylgeranylation catalyzes the transfer of a C20 geranylgeranyl group from geranylgeranyl pyrophosphate to proteins ending with the CAAL motif (C is cysteine, A is an aliphatic amino acid and L is leucine or phenylalanine). Geranylgeranylated proteins include, for example, RhoA, RhoC, Rap1, Ral, Rac, Cdc42, as well as gamma-subunit of heterotrimeric G-proteins.

Certain protein prenyltransferases, including GGTase I, RabGGTase and FTase, have been implicated in cancer processes. See Carrico et al. (2005) *Bioorg. Med. Chem.* 13, 677-688 and Peterson et al. (2006) *J Biol Chem.* 286, 25935-25946. Studies have also demonstrated the physiological significance of prenyltransferases, including protein geranylgeranylation, in cancer. Knockout mice specific for the beta-subunit of GGTase-I have been established, and the GGTase-I deficiency was shown to result in reduced K-ras-induced lung tumor formation and dramatically increased survival (Sjogren et al. (2007) *J. Clin. Invest.* 117, 1294-1304). Characterization of GGTase-I-deficient cells showed proliferation inhibition and accumulation of $p21^{CIP1/WAF1}$, pointing to the significance of GGTase-I in cell proliferation and cell cycle progression. GGTase-I deficiency reduced oncogenic K-ras-induced lung tumor formation in mice, pointing to the significance of inhibiting GGTase-I to block tumor formation. Recent studies also showed that a number of geranylgeranylated proteins play important roles in tumorigenesis and metastasis. In addition to RhoA and Cdc42 proteins (Lim et al. (2005) *Cancer Cell* 6, 533-545), RalA protein was recently found to be activated downstream of Ras in most pancreatic cancer cells harboring an oncogenic K-ras mutation. RalB plays critical roles in the survival pathway (Chien et al. (2003) *EMBO Rep.* 4, 800-806). RhoC is overexpressed in metastatic cancer and RhoC knockout mice exhibit defect in metastasis (Clark et al. (2000) *Nature* 406, 532-535; Hakem et al. (2005) *Genes and Develop.* 19, 1974-1979). Overexpression of Rab25 in breast and ovarian cancer cells has been reported, and this mutation is a determinant for aggressiveness of these cancers (Cheng et al. (2004) *Nat. Med.* 10, 1251-1256; Cheng et al. (2005) *Cancer Res.* 65, 2516-2519). Rab25 is also upregulated in prostate cancer and transitional-cell bladder cancer (Cheng et al. (2004), supra). Overexpression of other Rab proteins such as Rab5a and Rab7 in cancer has been reported (Croizet-Berger et al. (2002) *Proc. Nat. Acad. Sci. USA* 99, 8277-8282; He et al. (2002) *Gene Expr.* 10, 231-242).

Several geranylgeranyltransferase type I inhibitors (GGTIs) have been identified. Most of these are derived from the CAAL peptide. See, e.g, (a) Farnesyltransferase inhibitors in cancer therapy (eds. Sebti, S. M. and Hamilton, A. D.) Humana Press, (b) Oualid et al. (2005) *J. Comb. Chem.* 7, 703-713, (c) Carrico et at (2005) (supra), and (d) Peterson et al. (2006) (supra).

Studies in a parent of the present patent application, PCT/US2008/009106, incorporated by reference herein in its entirety, describe analyzing libraries of small molecules generated by combinatorial chemistry, constructed by phosphine catalysis of allenoate compounds, and identify a variety of small molecule chemical compounds which specifically inhibit GGTase I and/or RabGGTase, in some cases by competing with a substrate protein. The GGTI compounds block the protein modification and inhibit membrane association and function of, e.g., Ral, Rho and Rap subfamilies. The GGTI compounds were shown to inhibit the proliferation of a variety of human cancer cells, to cause $G_1$ cell cycle arrest and induction of $p21^{CIP1/WAF1}$, and to exhibit antitumor activity in mouse models.

There exists a need to develop efficient drug delivery systems that preferentially deliver to cancer cells and tumors molecules such as the GGTI and RabGGTase inhibiting compounds described by the present inventors.

DESCRIPTION

Figure 1:
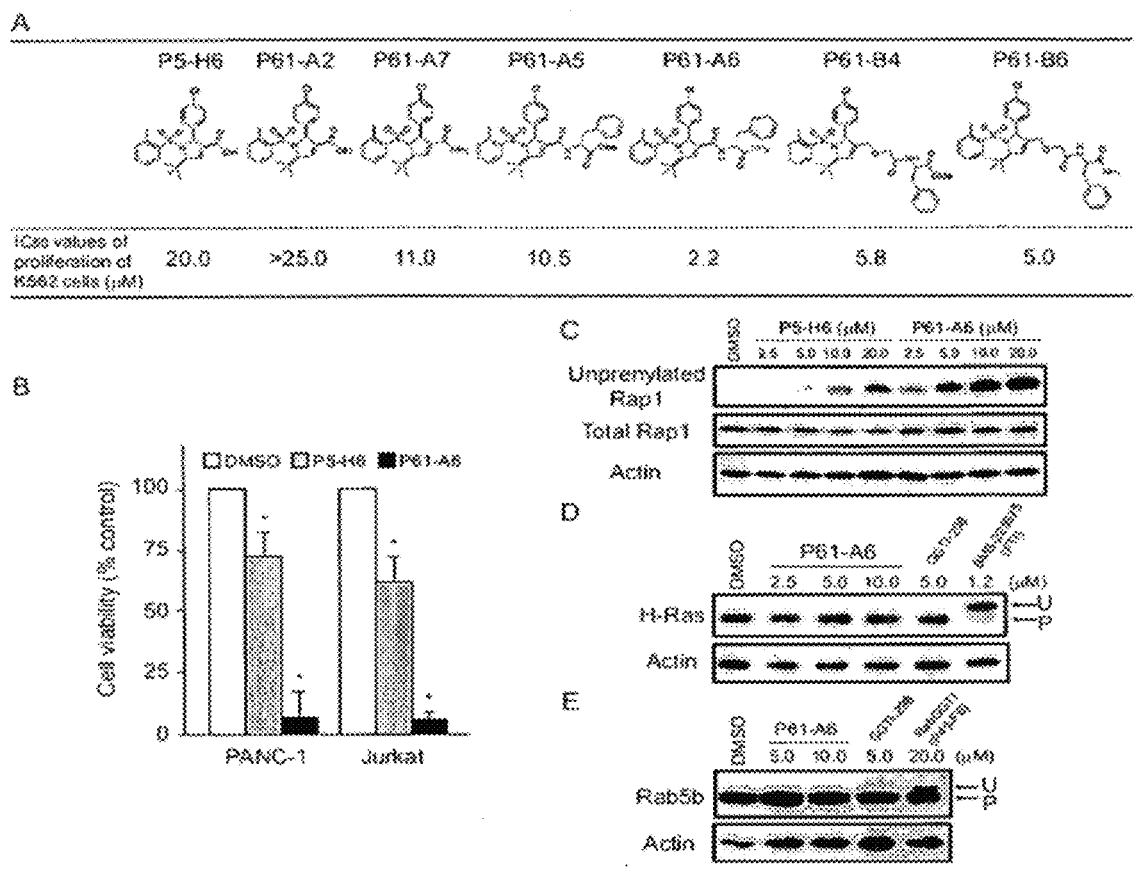
FIG. 1 shows the cellular activity of selected GGTI compounds. (A) shows the molecular structure of P5-H6 and modified P5-H6 compounds. K562 cells were treated with the modified compounds for 72 hours and then cell number was counted. $IC_{50}$ values of cell viability relative to the DMSO were measured. (B) shows the inhibitory effect of 12.5 µM P5-H6 or P61-A6 on PANC-1 and Jurkat cell viability. Data represent the mean+/−S.D. of two measurements from two independent experiments. *, P<0.05 compared with the value for DMSO. (C-E) P5-H6 or P61-A6 treatment inhibits Rap1 geranylgeranylation in NIH3T3 cells. Whole cell lysates from cells treated with DMSO, P5-H6, P61-A6, GGTI (GGTI-298), FTI (BMS-225975) or RabGGTI (P49-F6) for 48 hours were prepared and processed for immunoblot analysis using antibody against unprenylated form of Rap1 (C: upper panel), Total-Rap1 (C: middle panel), H-Ras (D: upper panel), Rab5b (E: upper panel) or actin (C, D, and E: lower panel). The immunoblots shown represent two independent experiments for each treatment.

The present application relates, e.g., to geranylgeranyltransferase type I inhibitors (GGTIs) which are encapsulated in (loaded into, incorporated in, associated with) one of several types of cancer-targeting liposomes. The liposomes encapsulating the GGTIs can be, e.g., basic liposomes (sometimes referred to herein as LipoGGTI), transferrin-conjugated liposomes (sometimes referred to herein as Tf-lipo-GGTI) or pH-sensitive liposomes (sometimes referred to herein as PH-Lipo-GGTI). It is to be understood that the discussion herein also relates to other compounds disclosed in PCT/US2008/009106 which are encapsulated in the liposomes, including molecules that inhibit RabGGTase.

The introduction of cancer targeting capability to the GGTI compounds by encapsulating them in the liposomes imparts a number of advantages, including high efficacy and low toxic side effects which result from introduction of the drug into non-cancer cells. Liposomes of the invention exhibit high levels of loading (encapsulation) capacity, cell internalization and intracellular drug release; are biocompatible and biogradable; are easily generated and manufactured; preferentially inhibit growth (proliferation) of cancer cells; and inhibit tumor growth. Without wishing to be bound by any particular mechanism, it is also suggested that the phospholipid bilayer structure of liposomes is appropriate for creating bio-related functions such as membrane destabilization and/or membrane fusion, and promoting cellular internalization of membrane-impermeable molecules across cellular membranes into cells.

One aspect of the invention is a liposome, which is
A basic liposome, or
a transferrin-conjugated liposome, or
a pH-sensitive liposome, wherein the liposome encapsulates (comprises, incorporates, is loaded with) a compound having the following formula (Formula I):

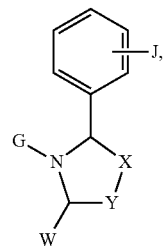

wherein J is hydrogen or is 1-2 substituents independently selected from the group consisting of halogen, $C_1$-$C_3$ alkyl, OR', SR', and NR'$_2$, where R' is alkyl.
wherein G is

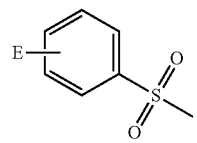

wherein E is hydrogen or is 1-2 substituents selected from the group consisting of halogen, $C_1$-$C_3$ alkyl, OR', SR', and NR'$_2$, where R' is alkyl, wherein W is selected from the group consisting of hydrogen, cyclic, linear, or branched alkyl of from 2 to 8 carbons, unsubstituted phenyl, and phenyl substituted with $C_1$-$C_3$ alkyl, halogen, OR', SR', and NR'$_2$, where R' is alkyl,

is selected from the group consisting of

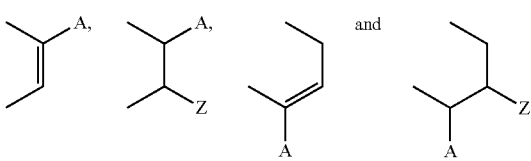

wherein A is selected from the group consisting of:

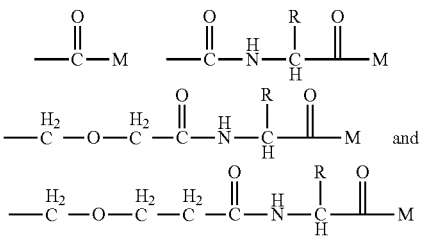

wherein M is selected from the group consisting of OH, OR'', NH$_2$, NHOH, NHOR'', wherein R'' is methyl or ethyl, or any other group that has a polar metal binder wherein R corresponds to an alpha-substituent of natural or non-natural alpha-amino acid;

wherein Z is S—U; and wherein U is selected from the group consisting of alkyl having 10 or fewer carbons, phenyl, optionally substituted with halogen or OR", wherein R" is methyl or ethyl, and $(CH_2)_n$—COOR$^4$, wherein n=1-4 and R$^4$ is a linear or branched alkyl having four or fewer carbons.

In embodiments of the invention,

A is

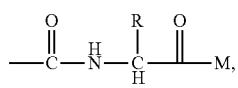

or

A is

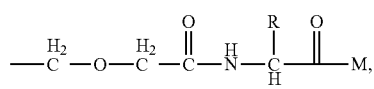

or

A is

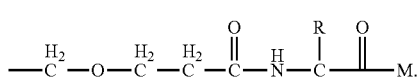

In embodiments of the invention, M is OEt, OMe, Ot-Bu, OH, NH2, NHOH, NHOMe, or any other groups that have a polar metal binder.

In embodiments of the invention, G is

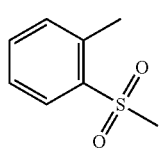

In embodiments of the invention, the compound is selected from the group consisting of

P61-A6

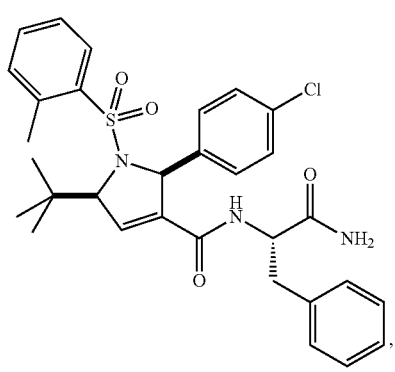

P61-A5

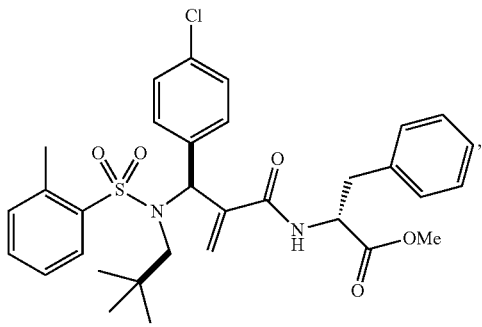

P61-B4

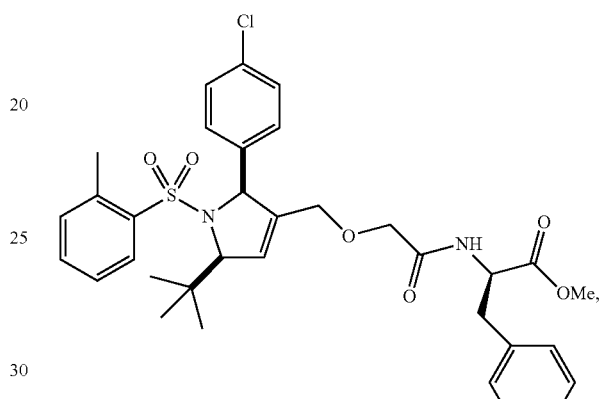

P61-B6

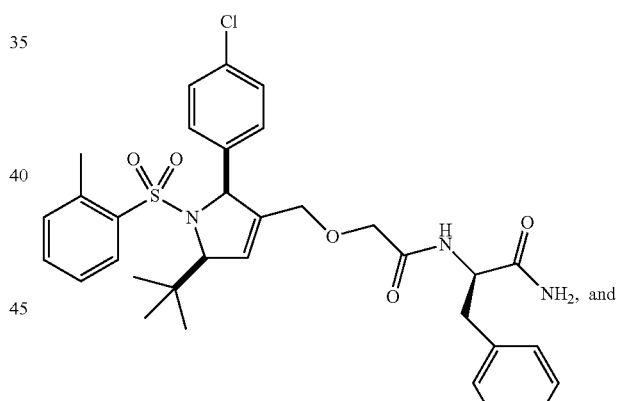

P61-E7

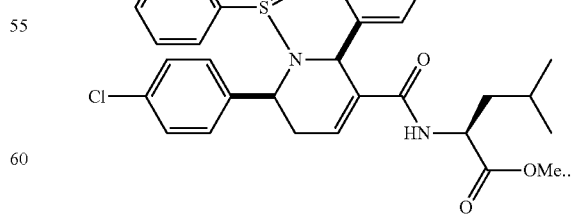

All five of the preceding compounds exhibit GGTI activity.

In embodiments of the invention, the liposome is a pH-sensitive liposome; the liposome comprises a molar ratio of the two lipids POPC and DSPE-PG8MG of about 85/15; and the liposome is sensitive to (releases its contents at) a pH of about 6.0 or lower.

In embodiments of the invention, the liposome inhibits the activity of a protein prenyltransferase, e.g., RabGGTase and/or GGTase I.

Another embodiment of the invention is a method comprising administering a liposome of the invention to a cell in an amount sufficient to inhibit the activity of GGTase I, or RabGGTase, or both GGTase I and RabGGTase. The liposome may be administered at a microgram/ml concentration, e.g., at a concentration of about 10-100 µg/ml.

Another embodiment of the invention is a method comprising administering a liposome of the invention in an amount sufficient to inhibit the growth (proliferation) of a cancer cell and/or to reduce the size of a tumor. The cancer cell or the tumor can be, e.g., pancreatic, leukemia, breast, lung, colon, ovarian, stomach, or prostate cancer. In one embodiment, the cancer cell comprises a GGTase I modified protein and/or a RabGGTase modified protein.

Another embodiment of the invention is a method comprising administering to a subject in need of treatment for a cancer a liposome of the present invention in an amount sufficient to inhibit the activity of a protein prenyltransferase (e.g., GGTase I, RabGGTase, or both). This method may further comprise administering to the subject an inhibitor of farnesyltransferase (FT), wherein the liposome and the FT inhibitor together are in an amount which is sufficient to inhibit the growth (proliferation) of a cancer cell and/or to reduce the size of a tumor (of cancer cells).

Another embodiment of the invention is a method comprising measuring the GGTase I and/or RabGGTase inhibiting activity of a liposome of the invention.

Another embodiment of the invention is a method for making (preparing) a liposome of the invention, using a method as described herein. For example, the method can comprise introducing (e.g. injecting) a solution comprising the compound (e.g. at about 2 mM) into a vessel containing a preformed liposome (e.g., a basic liposome, a transferrin-conjugated liposome, or a pH-sensitive liposome), collecting the loaded liposome by centrifugation, resuspending the collected liposome in a suitable buffer (such as PBS), filtering it, and applying it to a Sepharose 4B column.

Another embodiment of the invention is a kit comprising one or more liposomes of the invention, in a container.

Another embodiment of the invention is a method of delivering a pharmaceutical dosage form described herein, to a patient in need thereof, the method comprising:

registering in a computer readable storage medium the identity of a physician permitted to prescribe the pharmaceutical dosage form;

providing the patient with counseling information concerning a risk attendant to the pharmaceutical dosage form;

obtaining informed consent of the patient to receive the pharmaceutical dosage form despite the risk;

registering the patient in the computer readable medium after obtaining the informed consent; and permitting the patient access to the pharmaceutical dosage form (e.g. a prescription).

Another embodiment of the invention is a method of educating a consumer regarding the pharmaceutical dosage forms described herein, the method comprising distributing the oral pharmaceutical dosage form to a consumer with consumer information at a point of sale.

Another embodiment of the invention is compound or a salt thereof having the formula of compound P61-E7, or a pharmaceutical composition comprising the compound P61-E7 and a pharmaceutically acceptable carrier.

Studies in a parent of the present patent application, PCT/US2008/009106, described analyzing libraries of small molecules generated by combinatorial chemistry, constructed by phosphine catalysis of allenoate compounds, and identified and characterized a variety of small molecule chemical compounds which specifically inhibit GGTase I and/or RabGGTase and can, for example, inhibit the proliferation of a variety of human cancer cells and exhibit antitumor activity in mouse models. Some of this characterization is repeated herein. Compounds encompassed by Formula I are sometimes referred to herein as "compounds of the invention."

Described herein are formulations in which compounds of the invention are encapsulated in (encapsulated by) one of three types of liposomes: basic liposomes, transferrin-conjugated liposomes, and pH-sensitive liposomes. By "encapsulated" is meant herein that the liposomes comprise the compounds. Without wishing to be bound be any particular mechanism, the term "encapsulated" is meant to include compounds which are present, at least in part, in the aqueous interior of a liposome and/or in the lipid bilayer. The terms encapsulated, incorporated in, loaded into, and associated with, are used interchangeably herein. Liposomes comprising a compound of the invention are sometimes referred to herein as "liposomes of the invention." They are sometimes referred to as nano-formulated liposomes or nanoparticles.

Liposomes of the invention preferentially accumulate in tumors by the Enhanced Permeability and Retention (EPR) Effect and release their contents into the cancer cells. The EPR effect is a unique phenomenon of solid tumors related to their anatomical and pathophysiological differences from normal tissues. For example, angiogenesis leads to high vascular density in solid tumors, large gaps exist between endothelial cells in tumor blood vessels, and tumor tissues show selective extravasation and retention of macromolecular drugs. See Fang et al. (2011) *Advanced Drug Delivery Reviews* 63, 136-151 for a further discussion of the EPR effect.

The presence of transferrin which has been conjugated to liposomes enhances their tumor specificity and results in even more preferential killing of cancer cells. When pH-sensitive liposomes are used, the compounds are rapidly released in acidic environments such as intracellular lysosomes in tumors or tumor interstitial space.

Many of the Examples herein which are directed to liposomes describe experiments conducted with liposomes that encapsulate the GGTI compound, P61-A6. It is to be understood that the results presented in these Examples are also representative of studies with other protein prenyltransferase inhibitors, including other inhibitors of GGTase-I (GGTI), as well as compounds that inhibit RabGGTase or that inhibit both GGTase-I and RabGGTase. The studies presented herein show, e.g., that GGTI released inside of cells induces cell cycle arrest, expression of the cell cycle regulator P21(CIP1/WAF1) as well as unprenylated Rap1. Cell proliferation is also significantly inhibited by GGTI-loaded liposomes. Finally, the experiments show that the liposomal GGTI can be combined with FTI to inhibit K-Ras signaling in cancer cells, leading to even more cell proliferation inhibition. This opens up a new direction in the use of GGTI for cancer therapy.

There are several reasons why protein prenyltransferases such as GGTase I or RabGGTase are attractive targets for anti-cancer drug development. For example, Rho proteins such as RhoA and Rac are important for enhancing transformation. In fact, peptidomimetic inhibitors of GGTase I have shown promise in inhibiting proliferation of cancer cells. An arrest of the cell cycle at the GO/G1 phase was consistently observed with GGTase I inhibitors. Furthermore, one of the geranylgeranylated proteins, RhoC, has been identified as a protein involved in cancer metastasis. Therefore, blocking the function of RhoC by inhibiting its geranylgeranylation provides an effective way to inhibit metastasis. Furthermore, GGTIs are useful to inhibit alternative prenylation of K-Ras4B. GGTIs that specifically inhibit K-Ras4B geranylgeranylation but do not inhibit geranylgeranylation of RhoA are of interest, as they may provide a way to overcome one of the major shortcomings of currently available FTIs. While FTIs can potently inhibit FTase, they are incapable of inhibiting K-Ras, as this protein undergoes modification by GGTase I. See, e.g., Tamanoi et al. (2001) *Cell Mol. Life Sci.* 58, 1-14.

As used herein, the singular forms "a," "an," and "the" include plural referents unless the context clearly dictates otherwise. For example, "a" liposome includes one, two or more liposomes, which can be the same or different.

As used herein, the term "about" means plus or minus 10%. This refers, for example, to concentrations, percentages, weights, pH, numbers of units such as carbon molecules, or the like.

As used herein, the term "inhibit" means that a compound or liposome stops or otherwise prevents, to a measurable degree, at least one function of a target compound. For example, a GGTase I inhibitor can stop or otherwise prevent at least one activity a target compound, for example, an activity of the enzyme GGTase I. In some embodiments, the target compound for the inhibitors described herein is a protein prenyltransferase Inhibiton can occur in vitro and/or in vivo using a predetermined amount of an inhibitor.

As used herein, an agent that "specifically" inhibits GGTase I inhibits that enzyme preferentially (selectively) and generally does not inhibit other enzymes for which the inhibition is not intended. For example, GGTI inhibits GGTase-I with IC50 values of 300-400 nM. Even at 50,000 nM concentration, no significant inhibition was observed on the activities of two closely related enzymes, FTase and RabGGTase. An agent that "specifically" inhibits the proliferation of cancer cells inhibits the proliferation of cancer cells but does not inhibit, to a statistically significant level, the proliferation of non-cancerous cells. The parameters required to achieve such specific activities interactions can be determined routinely, using conventional methods in the art.

Chemical Definitions

Unless specified otherwise, the following chemical definitions are used throughout the sections below.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which may be attached to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like. "Bulky alkyl" includes cycloalkyl and branched chain alkyls with 4-8 carbons.

The term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl. "Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl." For example,

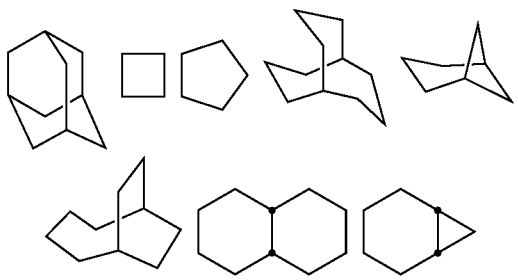

and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

The term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butyryl, 2-butyryl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

Salt, crystalline, and other forms of the chemical compounds depicted in the formulas and structures shown and described herein are contemplated within the meaning of "compound" of the invention. As one of skill in the art will appreciate, the compounds described herein may be used in their salt form (e.g., a sodium, potassium, or other pharmaceutically acceptable salt) or in a crystalline form. For some compounds, e.g., mP5-H6, a salt cannot be readily prepared using conventional methods but, as one of skill in the art will appreciate, alternative methods may be used to prepare a salt. The salt or crystalline forms of the compounds described herein may be useful as part of a pharmaceutical composition.

The term "halogen" or "halo" as used herein alone or as part of another group refers to chlorine, bromine, fluorine, and iodine.

The terms "halogenated alkyl", "halogenated alkenyl" and "alkynyl" as used herein alone or as part of another group refers to "alkyl", "alkenyl" and "alkynyl" which are substituted by one or more atoms selected from fluorine, chlorine, bromine, fluorine, and iodine.

The term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings).

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

The term "heterocyclic" or "heterocycle", as used herein, represents an unsubstituted or substituted stable 5- to 10-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl. The term "heterocyclic aromatic" as used here in alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

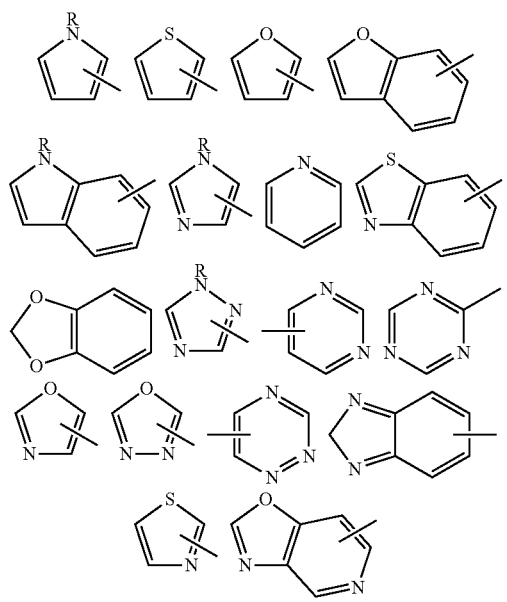

and the like.

The term "polar metal binder" means a polar group that is capable of binding, e.g., chelating, to a metal. Non-limiting examples have been disclosed in the chemical structures included in this application and its figures.

The compounds described herein, including those described in Formula I, can be made using a variety of synthesis methods which are described herein.

Assays for the Identification of Novel Inhibitors of Protein Geranylgeranyltransferase Type I Libraries were screened for inhibitors of protein geranylgeranyltransferase type I. Protein prenyltransferase assays were carried out by using filter binding. Two different substrates, RhoA and K-Ras4B, were used for the assay. RhoA ends with the CaaL motif and is an exclusive substrate for GGTase I, while K-Ras4B ends with the CaaX motif and is modified by both GGTase I and FTase. The presence of a polybasic domain consisting of a stretch of lysine close to the CaaX motif enables this CaaX motif to be recognized by GGTase I. Thus, RhoA and K-Ras4B are two very different substrates of this enzyme and it is of interest to identify small molecule inhibitors exhibiting preferential inhibition on reaction driven by one substrate over another.

GGTI Compounds

Through the library screening and other assays described herein, numerous compounds have been identified that can inhibit GGTase I. These compounds can have Formula I, as set forth previously herein.

In some embodiments, the GGTI compound can be selected from the following examples of GGTIs that have been made by the methods described herein.
P5-H6
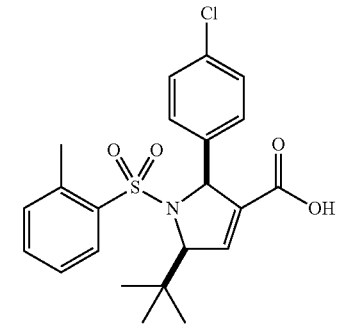
P61-A02
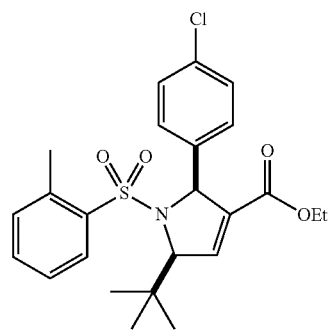
P09-C10
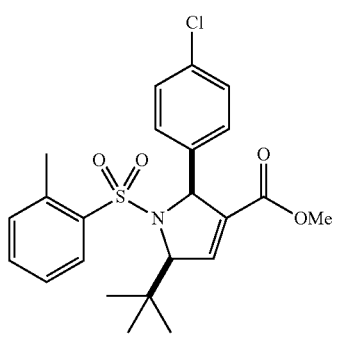
P61-A07
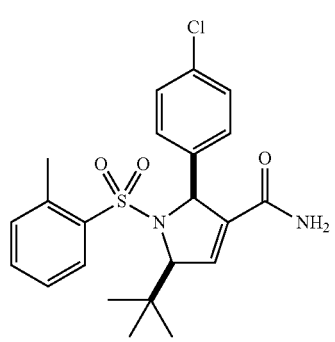
P61-C07
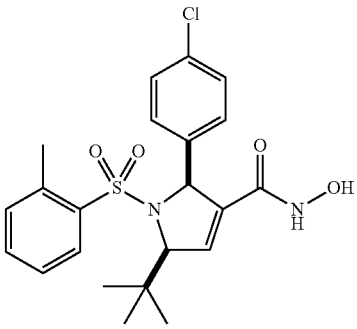
P61-E05
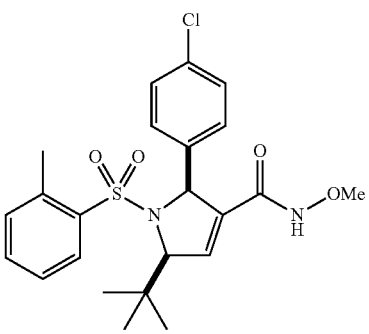
P61-A11
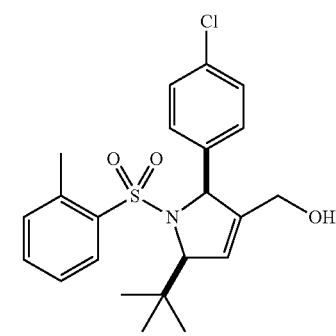
P03-E05
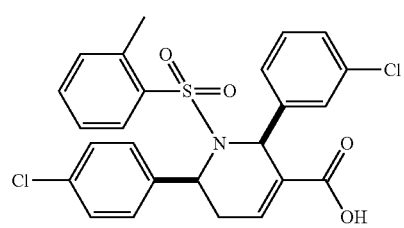
P67-C03
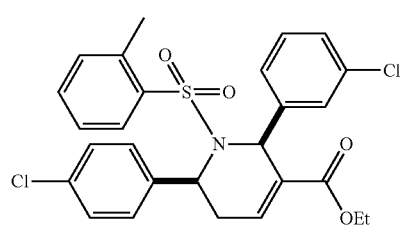

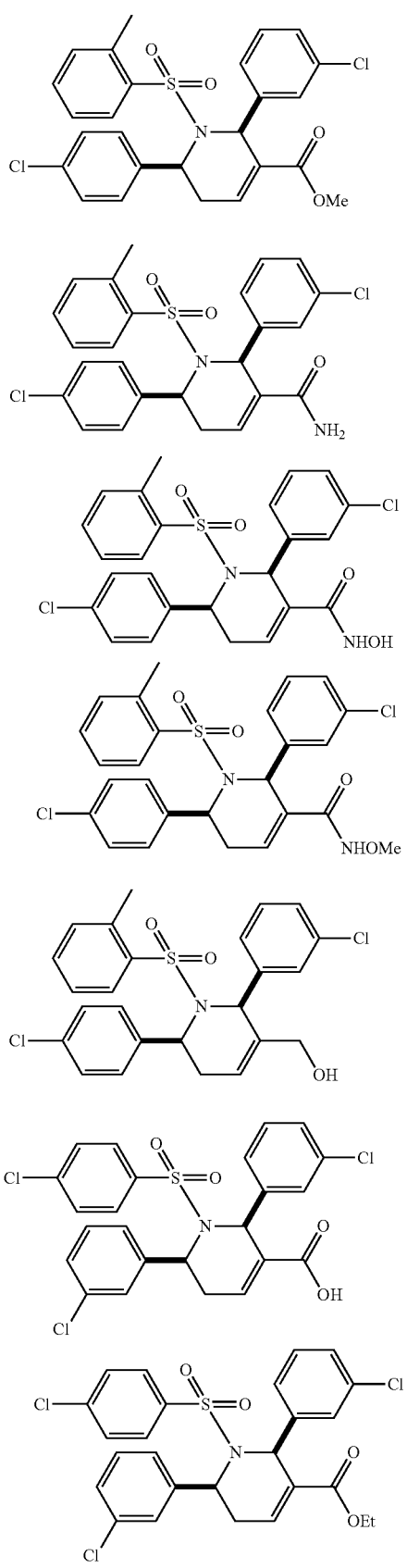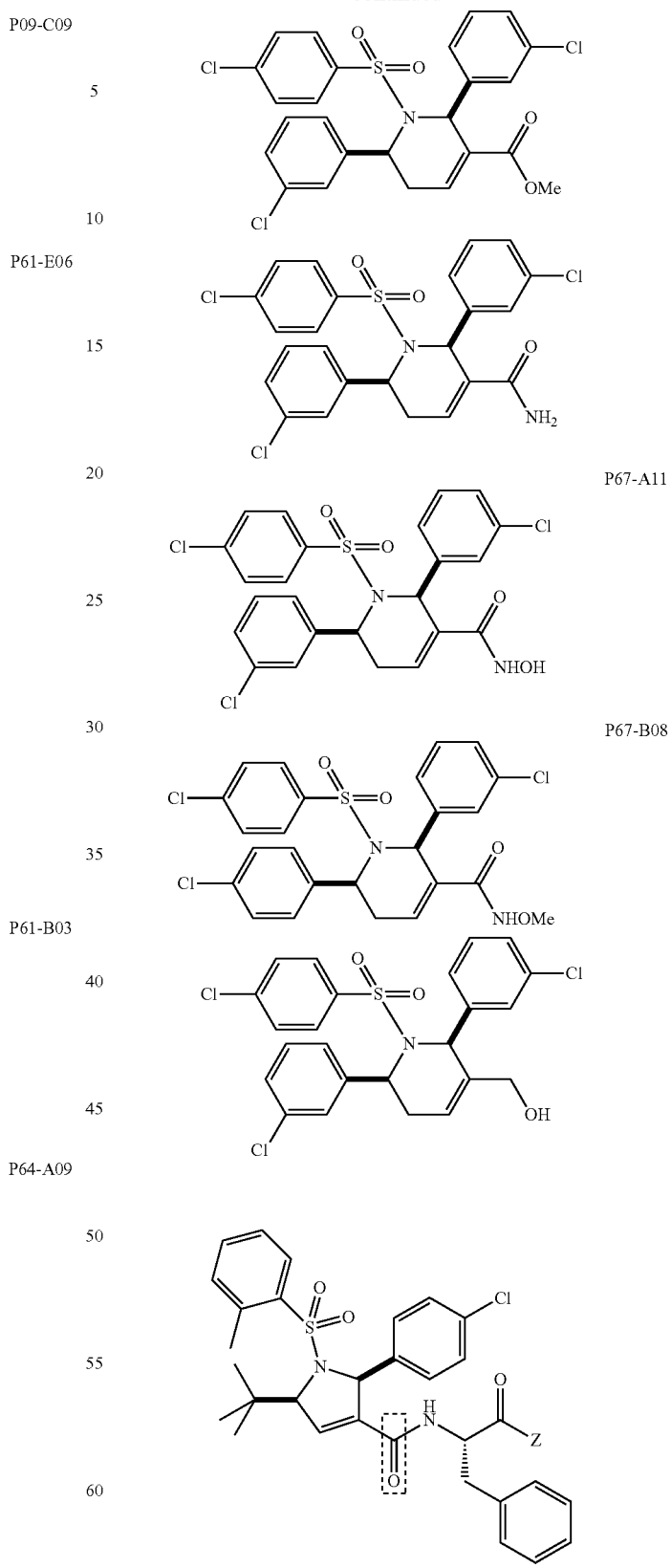
Z = OMe   P61A4 & P61A5
Z = OH    P61A8
Z = NH$_2$  P61A6 & P61B7

-continued
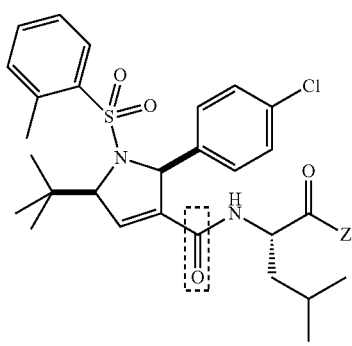
Z = OMe    P67B9
Z = OH
Z = NH₂    P61B2
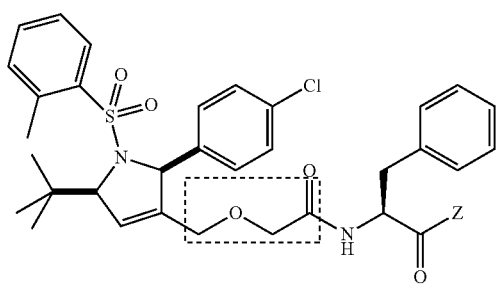
Z = OMe    P61B4
Z = OH     P61B5
Z = NH₂    P61B6
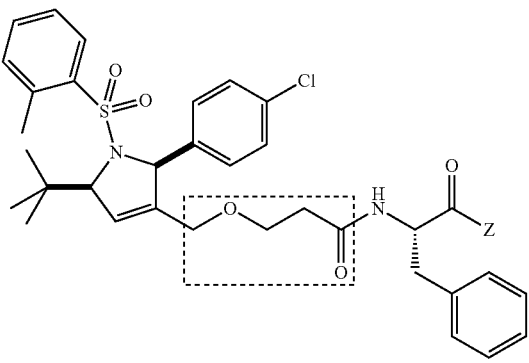
Z = OMe    P61E4
Z = OH
Z = NH₂
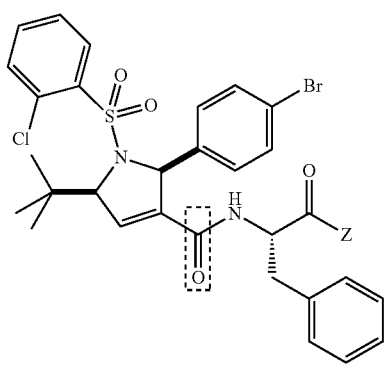
Z = OMe
Z = OH
Z = NH₂    P61B8 & P61B9
-continued
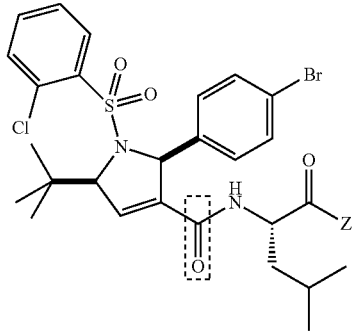
Z = OMe
Z = OH
Z = NH₂
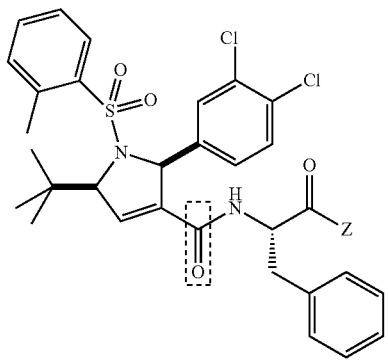
Z = OMe
Z = OH
Z = NH₂    P61B10 & P61B11
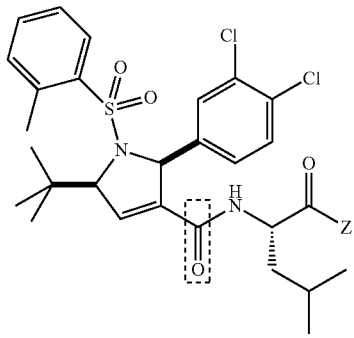
Z = OMe
Z = OH
Z = NH₂
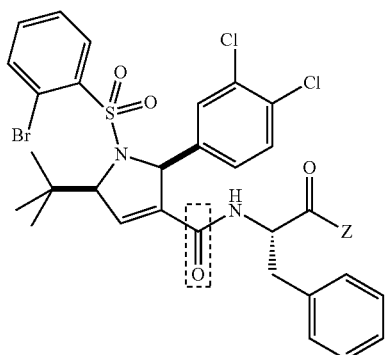
Z = OMe
Z = OH
Z = NH₂    P61E3

19
-continued
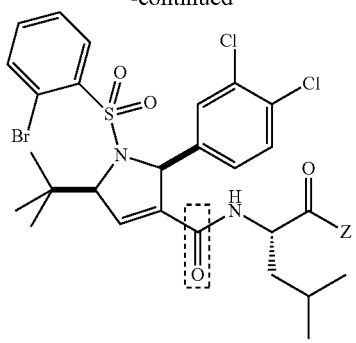
Z = OMe
Z = OH
Z = NH₂
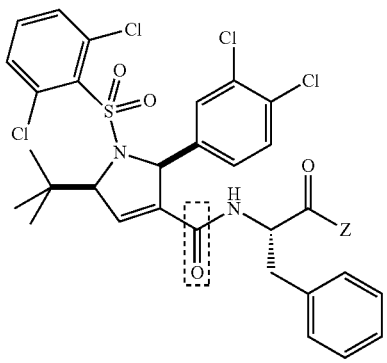
Z = OMe
Z = OH
Z = NH₂  P61D9 & P61D10
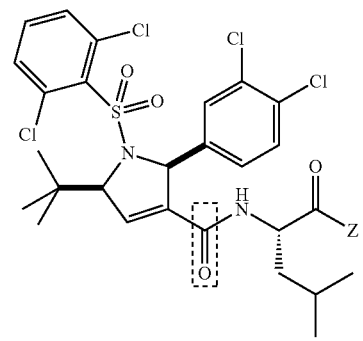
Z = OMe
Z = OH
Z = NH₂
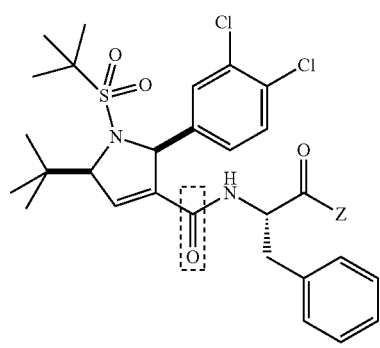
Z = OMe
Z = OH
Z = NH₂  P61D11 & P61E2
20
-continued
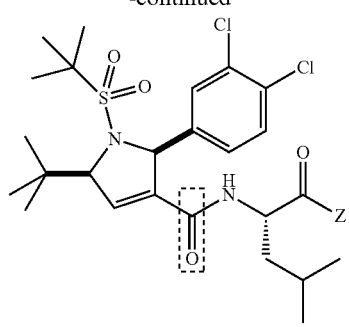
Z = OMe
Z = OH
Z = NH₂
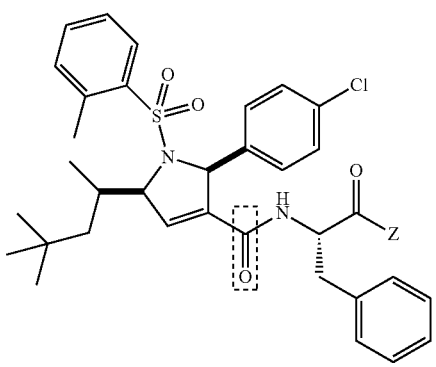
Z = OMe
Z = OH
Z = NH₂  P61C3 & P61C4
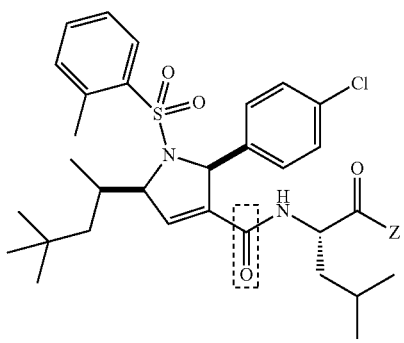
Z = OMe
Z = OH
Z = NH₂
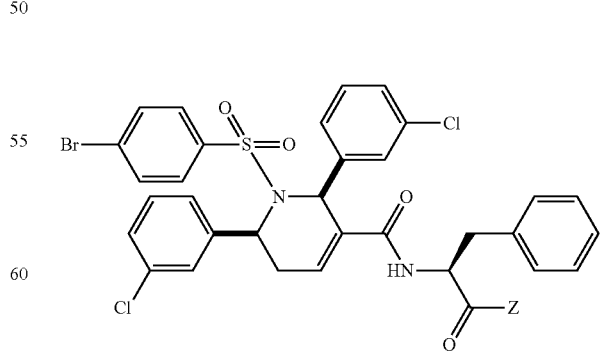
Z = OMe  P67-A08
Z = OH   P61-G05
Z = NH₂  P61-D04 & P61-D05

-continued
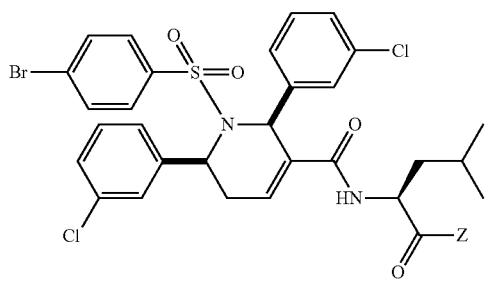
Z = OMe  P67-A09
Z = OH   P61-E11
Z = NH₂  P61-E08
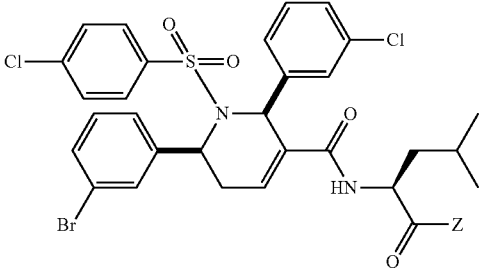
Z = OMe  P67-A07
Z = OH   P61-G08
Z = NH₂  P61-C06
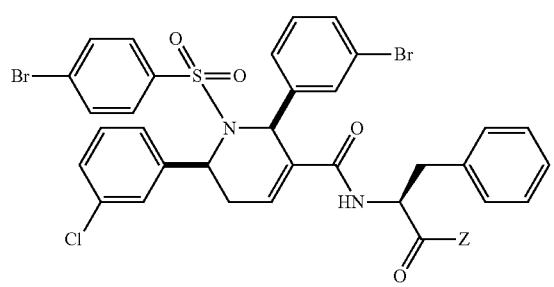
Z = OMe  P67-A03
Z = OH   P61-G06
Z = NH₂  P61-E09 & P61-E10
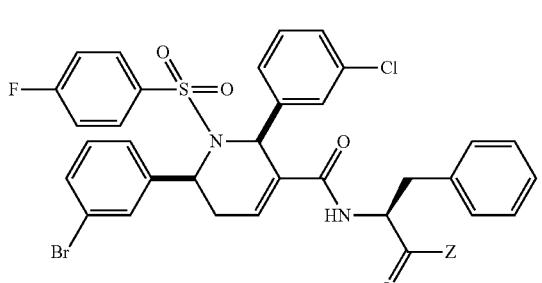
Z = OMe  P67-A06
Z = OH   P61-H07
Z = NH₂  P61-H04
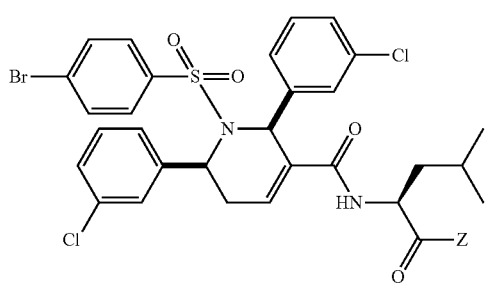
Z = OMe  P67-A04
Z = OH   P61-H03
Z = NH₂  P61-C09 & P61-C10
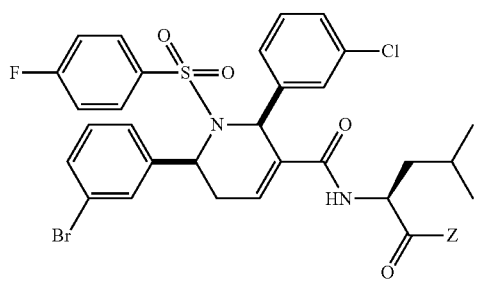
Z = OMe  P61-H11
Z = OH   P61-H06
Z = NH₂  P61-C11 & P61-D03
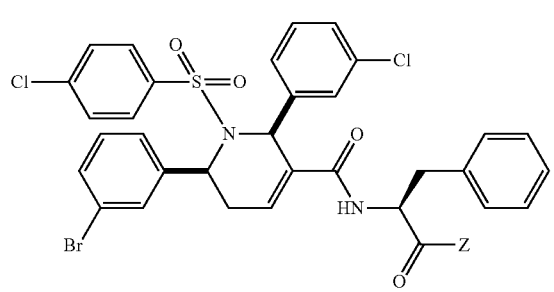
Z = OMe  P67-A10
Z = OH   P61-G07
Z = NH₂  P61-F11 & P61-G02
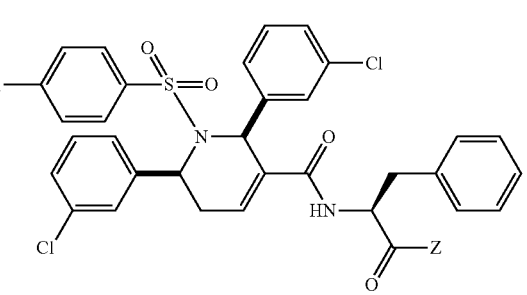
Z = OMe  P67-A02
Z = OH   P61-H09
Z = NH₂  P61-D02

-continued

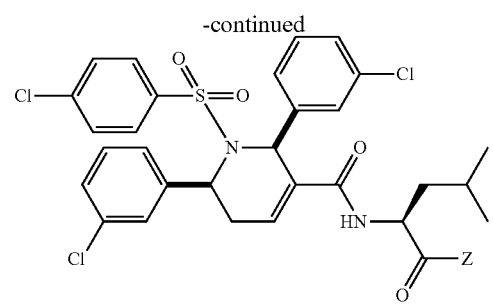

Z = OMe  P67-A05
Z = OH    P61-H08
Z = NH₂   P61H05

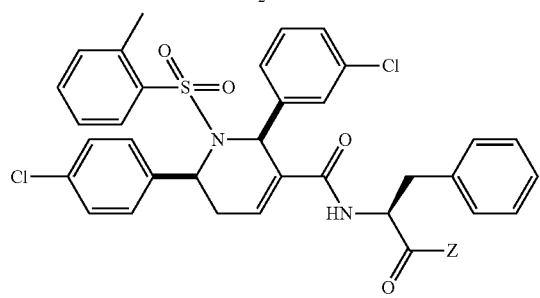

Z = OMe  P67-B02, P67-B03, P67-B04
Z = OH    P67-B06
Z = NH₂   P67-B05

-continued

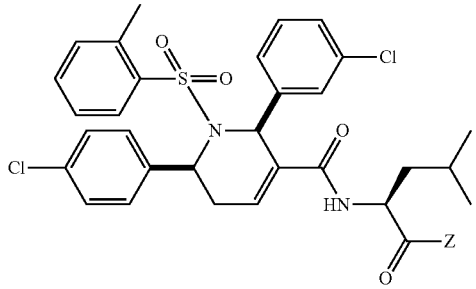

Z = OMe  P61-E07
Z = OH    P67-B07
Z = NH₂   P61-C05

Some exemplary compounds that inhibit GGTase I activity are listed in Tables 1, 2 and 3. In vitro $IC_{50}$ values for the GGTase I activity were obtained. In cell $GI_{50}$ values for the growth inhibition of a variety of cancer cell lines (e.g., Jurkat, K562, MDA-MB-231, BT474, MCF7, MiaPaCa2, Aspc-1, Panc-1, Capan-2, CFpac-1, and MCF10a) are reported below.

TABLE 1

P5-H06 with Different Linkers

| Structure | In vitro | Leukemic cells | | Breast Cancer Cells | | | | Pancreatic Cancer Cells | | | | |
| | | Jurkat | K562 | MDA-MB-231 | BT474 | MCF7 | MCF-10a | Mia-PaC a2 | Aspc-1 | Panc-1 | Ca-pan-2 | CF-pac-1 |
|---|---|---|---|---|---|---|---|---|---|---|---|---|
| P5-H6 | 0.5 | 20.00 | | | | | | | | | | |
| P61-A4 & P61-A5 | P61A4 >50  P61A5 >50 | P61A4 19.0  P61A5 10.5 | P61A4 14.0  P61A5 17.0 | | | | | | | | | |

TABLE 1-continued
P5-H06 with Different Linkers
| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF-10a | Mia-PaCa2 | Aspc-1 | Panc-1 | Ca-pan-2 | CF-pac-1 |
| 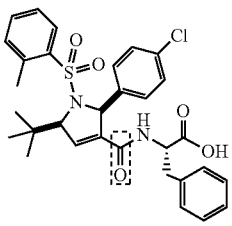 P61-A8 | 1.4 | 13.0 | 20.0 | | | | | | | | | |
| 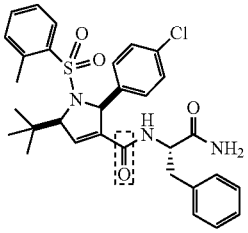 P61-A6 & P61-B7 | P61A6 1.0 P61B7 7.7 | P61A6 4.89 | P61A6 6.28 | P61A6 8.25 | P61A6 8.64 | P61A6 3.72 | P61A6 13.25 | P61A6 7.48 | P61A6 12.39 | P61A6 13.01 | P61A6 11.54 | P61A6 6.38 |
| 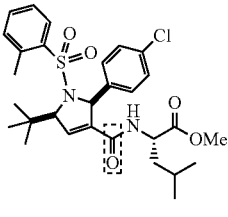 P67-B09 | | | | | | | | | | | | |
| 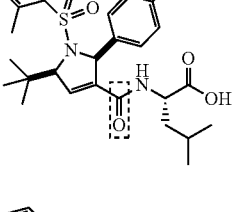 P61-B02 | 8.1 | 6.58 | 6.70 | 6.68 | 5.28 | | | 7.24 | 11.44 | 6.45 | 6.69 | <1.25 |

TABLE 1-continued

P5-H06 with Different Linkers

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF-10a | Mia-PaC a2 | Aspc-1 | Panc-1 | Ca-pan-2 | CF-pac-1 |
| P61-B4 | 2.1 | 3.51 | 6.01 | | | 6.78 | ~20 | | | | | |
| P61-B5 | 0.1 | 12.0 | 17.0 | | | | | | | | | |
| P61-B6 | 0.7 | 1.3 | 5.0 | | | | | | | | | |
| P61-E4 | >20 | 5.1 | | | | | | | | | | |

TABLE 2

Different Dihydropyrroles Coupled with L-Phenylalaninamide

| Structure | In vitro | Leukemic cells | | Breast Cancer Cells | | | | Pancreatic Cancer Cells | | | | |
| --- | --- | --- | --- | --- | --- | --- | --- | --- | --- | --- | --- | --- |
| | | Jurkat | K562 | MDA-MB-231 | BT474 | MCF7 | MCF-10a | Mia-PaCa2 | Aspc-1 | Panc-1 | Capan-2 | CF-pac-1 |
| P61-A6 & P61-B7 | P61A6 1.0 P61B7 7.7 | P61A6 4.89 | P61A6 6.28 | P61A6 8.25 | P61A6 8.64 | P61A6 3.72 | P61A6 13.25 | P61A6 7.48 | P61A6 12.39 | P61A6 13.01 | P61A6 11.54 | P61A6 6.38 |
| P61-B10 & P61-B11 | P61B10 5.4 P61B11 7.6 | P61B10 5.62 P61B11 6.90 | P61B10 6.74 P61B11 6.90 | P61B10 12.63 P61B11 5.54 | P61B10 10.81 P61B11 10.55 | P61B11 4.74 | P61B11 9.38 | P61B10 8.06 P61B11 7.49 | P61B10 12.92 P61B11 11.51 | P61B10 11.69 P61B11 7.52 | P61B10 8.45 P61B11 11.28 | P61B10 6.09 P61B11 2.03 |
| P61-E3 | >20 | | | | | | | | | | | |
| P61-B8 & P61-B9 | P61B8 6.0 P61B9 >10 | P61B8 4.74 P61B9 8.75 | P61B8 5.21 P61B9 9.18 | P61B8 4.43 P61B9 11.28 | P61B8 9.08 P61B9 9.90 | | | P61B8 6.15 P61B9 12.06 | P61B8 12.17 P61B9 16.83 | P61B8 9.05 P61B9 11.97 | P61B8 8.32 P61B9 10.69 | P61B8 6.16 P61B9 6.30 |

TABLE 2-continued

Different Dihyropyrroles Coupled with L-Phenylalaninamide

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF-10a | Mia-PaCa2 | Aspc-1 | Panc-1 | Capan-2 | CFpac-1 |
| P61-C3 & P61-C4 | P61C3 >10 P61C4 >50 | P61C3 9.79 P61C4 6.40 | P61C3 6.30 P61C4 5.95 | P61C3 10.81 P61C4 10.11 | P61C3 3.1 P61C4 4.71 | P61C3 9.16 P61C4 11.31 | P61C3 7.17 P61C4 6.70 | P61C3 11.43 P61C4 8.61 | P61C3 8.85 P61C4 8.60 | P61C3 10.45 P61C4 7.5 | P61C3 ~1.25 P61C4 ~1.25 | |
| P61-D9 & P61-D10 | P61D9 >50 P61D10 >50 | P61D9 4.91 P61D10 5.28 | P61D9 3.63 P61D10 3.67 | | | | | | | | | |
| P61-D11 & P61-E2 | P61D11 >50 P61E2 2.7 | P61D11 5.91 P61E2 4.57 | P61D11 5.90 P61E2 4.22 | | | | | | | | | |

TABLE 3

P3E5 with Different Linkers

| Structure | In vitro | Leukemic cells | | Breast Cancer Cells | | | | Pancreatic Cancer Cells | | | | |
|---|---|---|---|---|---|---|---|---|---|---|---|---|
| | | Jurkat | K562 | MDA-MB-231 | BT474 | MCF7 | MCF-10a | Mia-PaC a2 | Aspc-1 | Panc-1 | Capan-2 | CFpac-1 |
| P03-E05 | 0.31 | 20 | | | | | | | | | | |

TABLE 3-continued
P3E5 with Different Linkers
| | | | | Breast Cancer Cells | | | Pancreatic Cancer Cells | | | | |
|---|---|---|---|---|---|---|---|---|---|---|---|
| Structure | In vitro | Leukemic cells Jurkat | K562 | MDA-MB-231 | BT474 | MCF7 | MCF-10 a | Mia-PaC a2 | Aspc-1 | Panc-1 | Ca-pan-2 | CF-pac-1 |
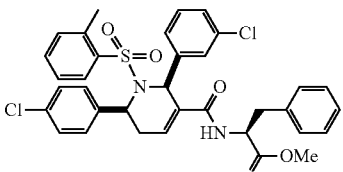
P67B2 & P67B3 & P67B4
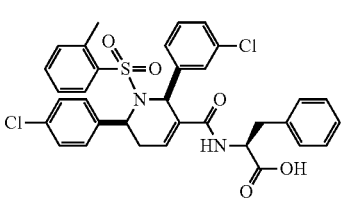
P67B6
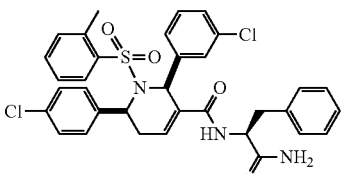
P67B5
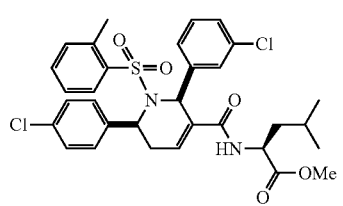
P61E7 — >50, 6.10
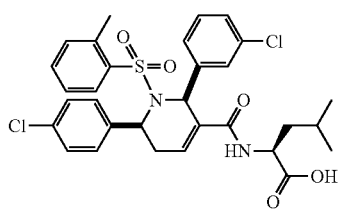
P67B7
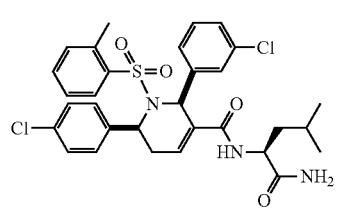
P61C5 — >50, 6.10, 6.15, , 10.86, >20, 11.99, , , 13.96, 13.69

TABLE 3-continued

P3E5 with Different Linkers

| | | Leukemic cells | | Breast Cancer Cells | | | Pancreatic Cancer Cells | | | | |
| --- | --- | --- | --- | --- | --- | --- | --- | --- | --- | --- | --- |
| Structure | In vitro | Jurkat | K562 | MDA-MB-231 | BT474 | MCF7 | MCF-10a | Mia-PaCa2 | Aspc-1 | Panc-1 | Ca-pan-2 | CF-pac-1 |

RabGGTase Inhibiting Compounds

In addition to or alternatively to GGTase I inhibition, protein prenyltransferase inhibiting compounds described herein can be effective as inhibitors of RabGGTase. Some of these compounds can exhibit dual specificity and can inhibit both RabGGTase and GGTase I. Compounds exhibiting these activities can also be encapsulated into liposomes and used as described herein Prior to the present compounds, only a handful of RabGGTase inhibitors had been identified. Commonly used inhibitors are bisphosphonate type compounds, however the inhibition of RabGGTase requires about mM concentration of the compounds. In contrast, in some embodiments, the compounds described herein suprisingly inhibit RabGGTase at a µM concentration. Accordingly, the RabGGTase inhibitors can be used at a concentration of about 1 µM up to about 50 µM, for example at concentrations between 1 µM and 25 µM.

Recent studies suggest that RabGGTIs may be valuable as anticancer drugs. A study using siRNA showed that the inhibition of RabGGTase leads to apoptosis induction in human cancer cells; elevated levels of RabGGTase are detected in a number of human cancers; and FTI compounds which inhibit RabGGTase induce mislocalization of Rab protein and apoptosis (Olson et al. (1998) *Nature* 394, 295-299). Accordingly, these compounds can be useful as cancer therapeutics.

One of skill in the art will appreciate that compounds described as GGTase I inhibitors or RabGGTase inhibitors are not limited to only that characterization. For example, as described herein, a compound can have dual specificity to inhibit both GGTase I and RabGGTase. Therefore, as one of skill in the art will appreciate, the compounds described herein are protein prenyltransferase inhibitors capable of inhibiting GGTase I, RabGGTase, other protein prenyltransferases, and combinations thereof.

Synthesis Methods

The compounds described herein can be made using any method known to one of skill in the art or as described herein. For example, a compound of Formula I can be synthesized by reacting a compound according to formula I'

I' wherein
J, G, and W are as defined above and

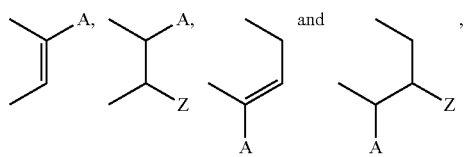

is selected from the group consisting of

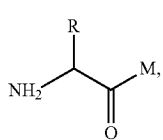

wherein A=CO$_2$H;
with a compound having the formula

wherein R and M are as defined above.

In one embodiment of the invention, p61-A4 or P61-A6 are prepared using the following example reaction scheme:

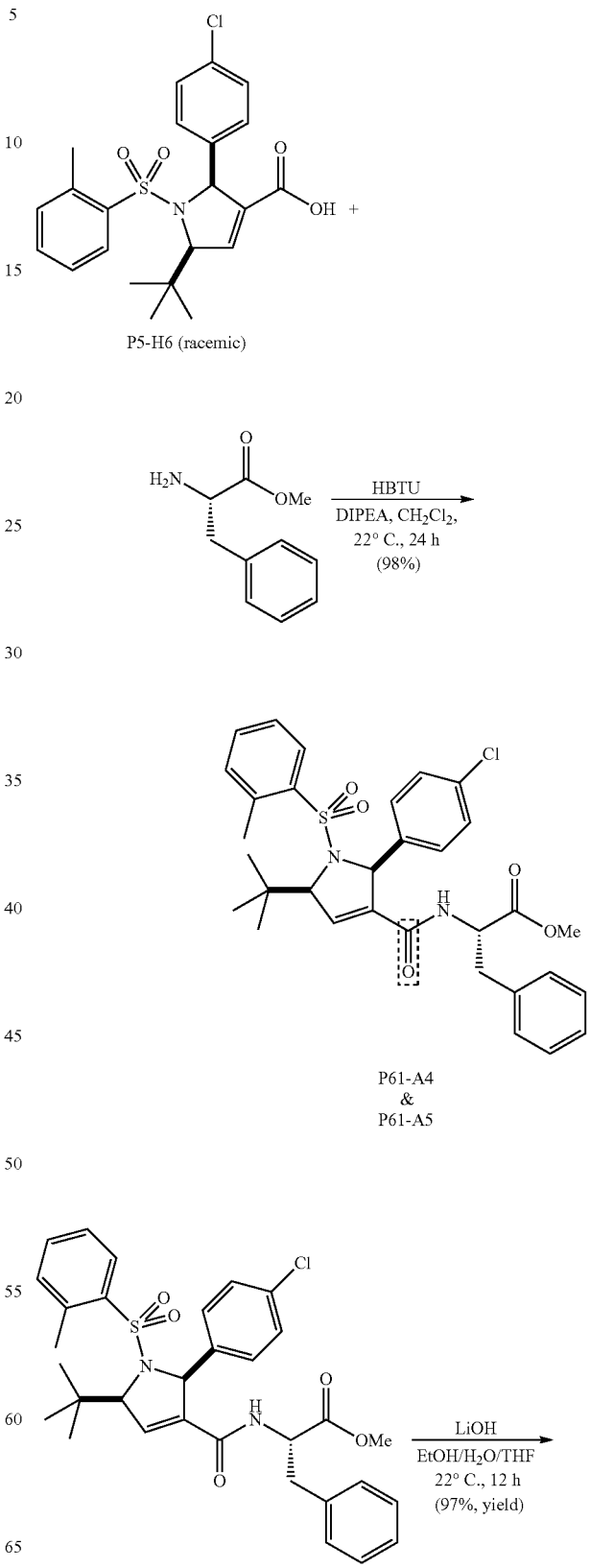

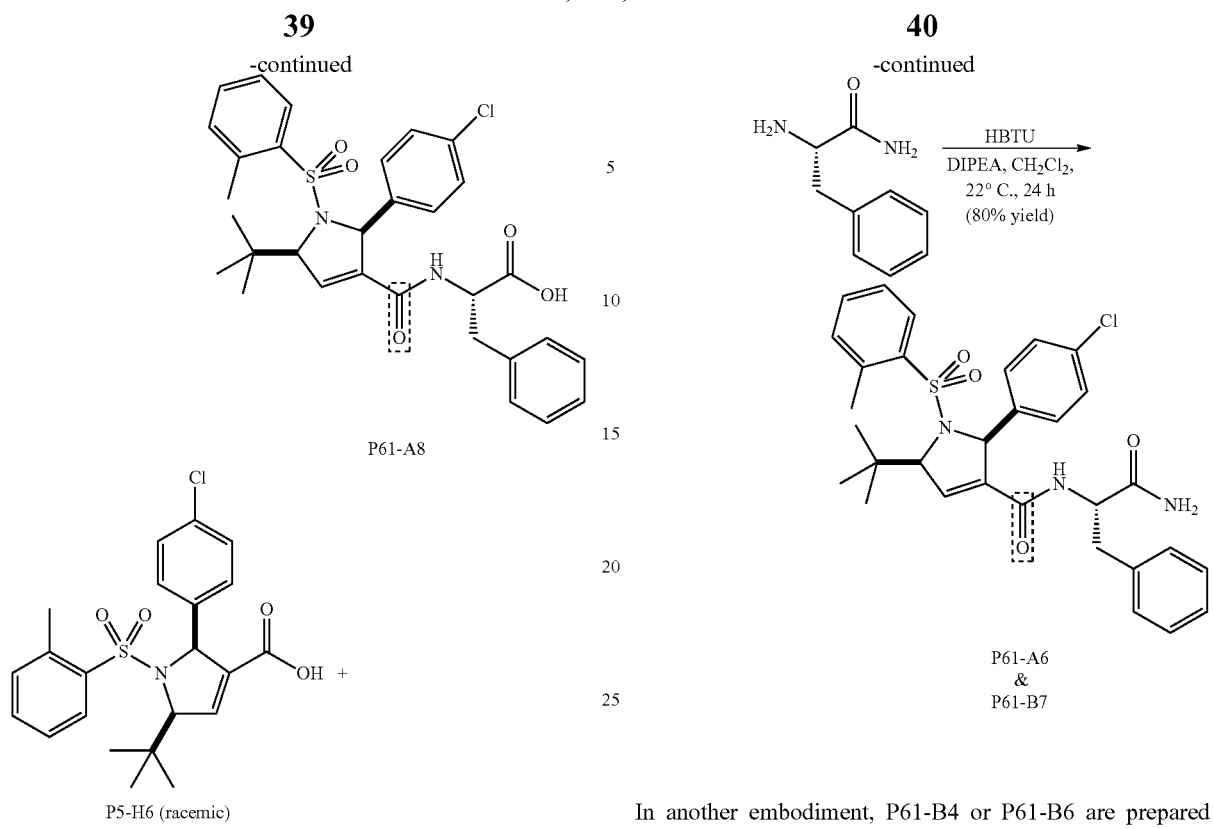
P61-A8
P5-H6 (racemic)
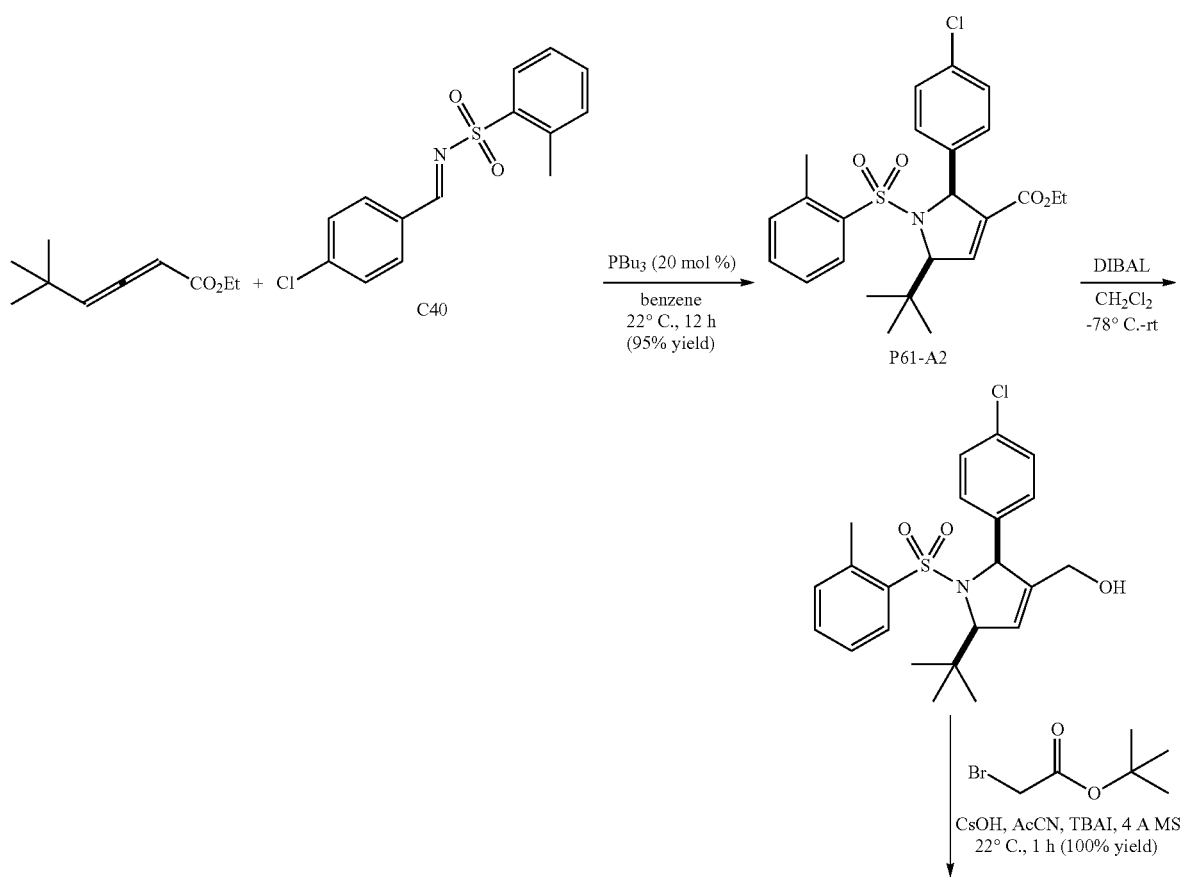
P61-A6 & P61-B7
In another embodiment, P61-B4 or P61-B6 are prepared using the following example reaction scheme:

-continued

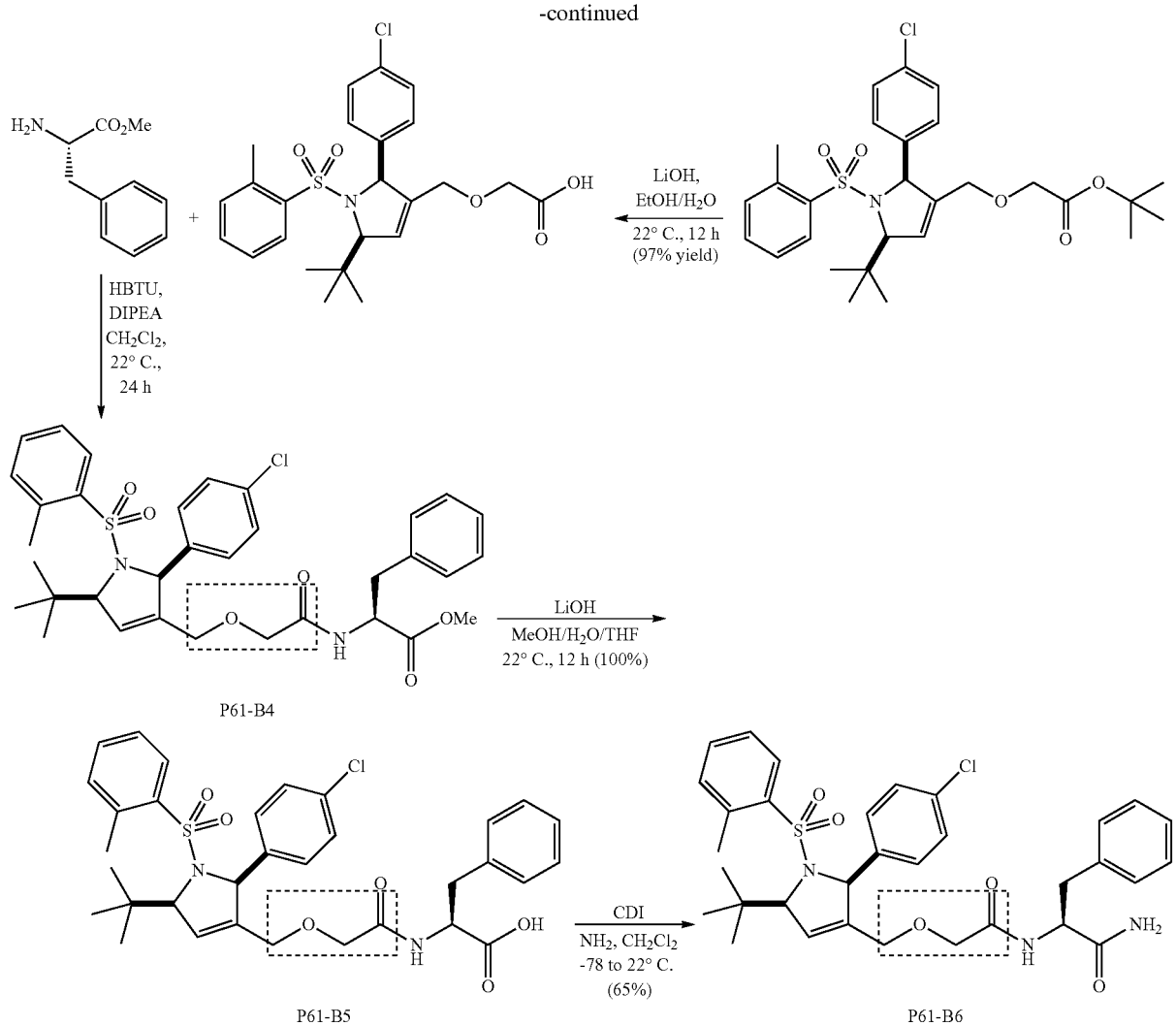

As one of skill in the art will appreciate, synthesis methods other than those disclosed may be used to produce the compounds of the present invention. Such methods are also encompassed by the present invention.

Therapeutic Formulations and Pharmaceutical Compositions

The compounds and liposomes of the invention are useful as therapeutically effective pharmaceutical compositions (therapeutic formulations, pharmaceutical dosage forms). A pharmaceutical composition of the invention can be prepared with a therapeutically effective amount of a compound of the invention and a pharmaceutically acceptable carrier or diluent, as defined herein. A therapeutic formulation of a liposome can be prepared by loading (encapsulating) a therapeutically effective amount of a compound of the invention within a liposome as described herein.

The compounds or liposomes of the invention can be formulated as pharmaceutical compositions (therapeutic formulations) and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the compounds or liposomes include, lozenges, troches, tablets, capsules, effervescent tablets, orally disintegrating tablets, floating tablets designed to increase gastric retention times, buccal patches, and sublingual tablets.

The compounds or liposomes of the invention may be systemically administered, e.g., orally, in combination with a pharmaceutically acceptable vehicle such as an inert diluent or an assimilable edible carrier, or by inhalation or insufflation. They may be enclosed in coated or uncoated hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. For compositions suitable for administration to humans, the term "excipient" is meant to include, but is not limited to, those ingredients described in Remington: The Science and Practice of Pharmacy, Lippincott Williams & Wilkins, 21st ed. (2006) (hereinafter Remington's), which is herein incorporated by reference in its entirety.

The compounds or liposomes may be combined with a fine inert powdered carrier and inhaled by the subject or insufflated. Such compositions and preparations should contain at least 0.1% compounds. The percentage of the compositions and preparations may, of course, be varied and may conveniently be between about 2% to about 60% of the weight of a given unit dosage form. The amount of compounds or liposomes in such therapeutically useful compositions is such that an effective dosage level will be obtained.

The tablets, troches, pills, capsules, and the like may also contain the following: binders such as gum tragacanth, *acacia*, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials may be present as coatings or to otherwise modify the physical form of the solid unit dosage form. For instance, tablets, pills, or capsules may be coated with gelatin, wax, shellac or sugar and the like. Of course, any material used in preparing any unit dosage form should be pharmaceutically acceptable and substantially non-toxic in the amounts employed.

In addition, the compounds or liposomes may be incorporated into sustained-release preparations and devices. For example, the compounds may be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The compounds or liposomes may also be administered intravenously or intraperitoneally by infusion or injection. Solutions of the compounds or liposomes can be prepared in water or a suitable buffer, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

A liposome which encapsulates a compound of the invention can take any of a number of forms. For example, three exemplary forms of liposomes are described herein: (1) basic liposomes, which are unilamellar phospholipid liposomes having a lipid bilayer and an aqueous interior. In one embodiment of the invention, such unilamellar phospholipid liposomes are provided as a dry powder that can readily encapsulate chemical compounds when resuspended in a buffer solution. (2) liposomes which have been conjugated, using conventional, art-recognized methods, to a tumor targeting moiety, such as transferrin or other such moieties that are well-known to those of skill in the art; and (3) pH-sensitive liposomes. As used herein, a "pH-sensitive liposome" refers to a liposome that is sensitive to low pH and releases contents loaded therein at a pH of about 7 or lower (e.g., at a pH about of about 6.5 or lower, or at a pH of about 6.0 or lower, or at a pH of about 5.5 or lower). In one embodiment of the invention, the contents of the liposome begin to be released at a pH of between about 5.5 and about 6.0. In one embodiment of the invention, the pH-sensitive liposome comprises two lipids—Palmitoyl oleoyl PC (POPC) and DSPE-PG8MG—at a molar ratio of about 85/15. pH-sensitive liposomes of the invention contain pH-sensitive fusogenic polymer moieties connected to phophatidylethanolamine group, producing highly pH-sensitive liposomes that are stable at neutral pH and destabilize in response to acidic pH.

Methods of making (loading) liposomes of the invention are described elsewhere herein, e.g. in the Examples. Compounds of the invention, such as GGTI, are encapsulated into the liposomes with greater than about 65-70% efficiency.

Optionally, the liposomes can be stabilized or fortified by any of a variety of conventional, art-recognized procedures. For example, cholesterol can be intercalated into the bilayer membrane; the liposome can be coated with a polysaccharide; the surface of the liposome can be PEGylated; or polymerized liposomes can be used.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the compounds or liposomes in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

For topical administration, the compounds or liposomes may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds or liposomes to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820, 508), all of which are hereby incorporated by reference.

Useful dosages of the compounds or liposomes of the invention can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds or liposomes in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

The amount of the compounds required for use in treatment will vary not only with the particular salt selected but also with the route of administration, the nature of the condition being treated and the age and condition of the patient and will be ultimately at the discretion of the attendant physician or clinician.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

In some embodiments, the pharmaceutical compositions described herein contain a therapeutically effective dose of the compound. The term "effective amount" or "therapeutically effective amount," as used herein, refers to the amount of the active compound that is effective to achieve its intended purpose after a single dose, wherein a single dose comprises one or more dosage units, or after a course of doses, e.g., during or at the end of the treatment period. Thus, for example, the term "therapeutically effective amount" of the compounds disclosed herein, when used in a method of treating a cancer, refers to that dose of the compound that lessens, at least to a measurable degree, or prevents the occurrence of cancer when administered to a mammal in need of such treatment. The therapeutically effective amount will vary depending on the needs of the subject, but this amount can readily be determined by one of skill in the art, for example, a physician.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 5 mg/kg, 10 mg/kg, or more of body weight per day.

The compounds or liposomes are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 1 mg, about 10 mg, about 25 mg, about 50 mg, about 75 mg, about 100 mg, about 150 mg, about 200 mg, about 250 mg, about 300 mg, about 350 mg, about 400 mg, about 450 mg, about 500 mg, about 750 mg, or about 1000 mg of active ingredient.

The compounds or liposomes can be administered to achieve peak plasma concentrations of, for example, from about 0.5 to about 75 µM, about 1 to 50 µM, about 2 to about 30 µM, or about 5 to about 25 µM. Exemplary desirable plasma concentrations include at least or no more than 0.25, 0.5, 1, 5, 10, 25, 50, 75, 100 or 200 µM. For example, plasma levels may be from about 1 to 100 micromolar or from about 10 to about 25 micromolar. This may be achieved, for example, by the intravenous injection of a 0.05 to 5% solution of the compounds, optionally in saline, or orally administered as a bolus containing about 1-100 mg of the compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the compounds per kg of body weight.

The compounds or liposomes may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator.

Methods of Treating, Assays, and Kits

Some embodiments of the present invention are directed to methods of using the compounds or liposomes described herein. These compounds or liposomes, as illustrated in the examples below and throughout the specification, are useful for inhibiting the geranylgeranylation of signaling proteins by inhibiting the activity of at least GGTase I and/or RabG-GTase. However, because GGTIs such as those described herein can inhibit geranylgeranylation of a number of signaling proteins, the compounds and liposomes described herein are effective for the treatment of a wide range of human cancers. For example, mP5-H6 inhibits proliferation of a leukemic cell line (Jurkat), breast cancer cell lines (BT474 and MDA-MB231) and pancreatic cancer cell lines (Panc-1 and MiaPaCa2).

Pancreatic cancer is of particular interest, as recent studies (Lim, K-H et al., *Current Biology* 16, 2385; Lim, K-H et al., *Cancer Cell* 7, 533) have established the importance of RalA and RalB proteins (both are geranylgeranylated) in pancreatic cancer. RalA is commonly activated in a panel of cell lines from pancreatic cancer. Studies using siRNA showed that inhibition of RalA reduced tumor growth. RalB is found to be important for metastasis. Interestingly, the RalA activation occurs downstream of K-ras activation that is seen in more than 80% of pancreatic cancer cases. Since K-ras prenylation can be inhibited by the combination of GGTI and FTI, GGTIs may be important for treating pancreatic cancer.

Breast cancer is also of interest, as GGTIs have been shown to inhibit proliferation of breast cancer cells (Vogt, A. et al., *J. Biol. Chem.* 272, 27224). This is accompanied by the accumulation of G1 phase cells and the increase of p21. In addition, a geranylgeranylated protein Rac3 is reported to be overactivated in breast cancer cells (Mira J-P et al., *PNAS* 97, 185). Finally, inhibition of RhoA or RhoC by siRNA inhibited proliferation and invasiveness of breast cancer cells in vitro and in vivo (Pille, J-Y et al., *Molecular Therapy* 11, 267).

GGTIs and/or RabGGTase inhibitors may also be valuable in inhibiting cancer metastasis. This is based, in part, on findings that indicate geranylgeranylated proteins play important roles in metastasis. In addition to RalB discussed above, another geranylgeranylated protein RhoC plays essential roles in cancer metastasis (Hakem A. et al., *Genes & Dev.* 19, 1974; Clark, E. A. et al., *Nature* 406, 532).

Accordingly, the compounds and liposomes described herein can be used in methods of treating cancer and/or in methods of reducing the size of a cancerous tumor. In some embodiments, the method of treating cancer involves inhibiting a protein prenyltransferase by administering the compound described herein to a subject in need of treatment. The methods of treating cancer can be applied to any cancer that is activated through a signaling pathway incorporating GGTase I and/or RabGGTase, for example Rho protein activation, e.g., RhoA and Rac in cancer cells. In some embodiments, the cancer is selected from the group consisting of pancreatic, leukemia, breast, and prostate. In some embodiments, the cancer is selected from the group consisting of pancreatic, leukemia, breast, prostate, colon, ovarian, lung, and stomach cancer.

The compounds and liposomes described herein are also useful in methods of inhibiting the activity of GGTase I and/or RabGGTase by administering the compounds or liposomes described herein to a cell. These methods can be applied either in vivo or in vitro. For example, these compounds can be used for therapeutic purposes associated with inhibiting the activity of GGTase I and/or RabGGTase in a subject in need of treatment thereof. These compounds can also be used in research methods designed to develop such therapeutics, for example, as part of a library screening as described herein.

The compounds and liposomes described herein are also useful in methods of cytostatically inhibiting the growth of a cancer cell. These methods can be used as a stand alone therapeutic or in conjunction with a cytotoxic treatment or a surgical procedure. The compounds and liposomes described herein can be administered following surgery to remove a tumor or following chemotherapy designed to kill the tumor cells to control the growth of any cancer cells that these treatments may have missed. These compound and liposomes, when administered in these embodiments, may function as a preventative measure designed to reduce the likelihood of remission.

The compounds and liposomes described herein are also useful for treating cancers when combined with another anticancer agent, such as a farnesyltransferase inhibitor (FTI). Ras family proteins, such as K-Ras, can be alternatively prenylated by either GGTase or FTase. Blockage of either enzyme individually generally cannot achieve complete inhibition of protein lipid modification, leading to an unsatisfactory clinical outcome for cancer therapy. But blockages of both enzymes at the same time can cause severe toxicity to other normal tissues, because the Ras family is critical for a number of cellular functions. Therefore, preferential and exclusive delivery of GGTI to tumors by using liposomes allows one combine these two types of compounds at the same time for cancer treatment without severe undesired side effects to noncancerous tissues. Such a combined use of a GGTI liposome with an FTI to inhibit K-ras signaling is particularly effective for treatment of a tumor in which K-ras is mutated, such as many pancreatic, lung and colon cancers. The two agents can be administered sequentially, in any order, or at the same time. Such a combined administration is also useful for overcoming B-Raf inhibitor resistance encountered during melanoma treatments.

The compounds and liposomes herein are also useful in assays for measuring the GGTase I and/or RabGGTase inhibiting activity of a compound. For example, the compounds and liposomes disclosed herein can be used as controls to evaluate new compounds for potential GGTase I and/or RabGGTase inhibiting activity. The compounds disclosed herein can be used as part of assays to determine therapeutic compounds for use in the methods disclosed herein as well.

The invention also provides kits comprising a compound or liposome of the invention, e.g. in the form of a pharmaceutically acceptable dosage form or as a compound or liposome These kits can include one or more containers filled with one or more of the ingredients of the pharmaceutical dosage forms.

In some embodiments, the kit comprises a container for the dosage form or compound or liposome. Suitable containers include, for example, a bottle, a box, a blister card, a foil packet, or a combination thereof. Optionally, the kit also contains directions for properly administering the dosage form or for properly using the compound, for example, as part of an assay. The kits can also be designed in a manner such that they are tamper resistant or designed to indicate if tampering has occurred. Optionally, the kit can contain the dosage form or compound or liposome with another pharmaceutical composition or compound or liposome, for example, an FTI.

Optionally associated with the container(s) in the kits can be a notice or printed instructions. Such printed instructions can be in a form prescribed by a governmental agency regulating the manufacture, use, or sale of pharmaceuticals or biological products, which notice reflects approval by the agency of the manufacture, use, or sale for human administration to treat a condition that could be treated by the compounds and dosage forms described herein. In some embodiments, the kit further comprises printed matter, which, e.g., provides information on the use of the dosage form to treat a condition or disease or a pre-recorded media device which, e.g., provides information on the use of the dosage form to treat a condition or disease, or a planner, integrally linked to the particular methods of using the compositions.

"Printed matter" can be, for example, one of a book, booklet, brochure or leaflet. The printed matter can describe the use of the dosage forms described herein to treat a condition or disease, for example, to treat a cancer involving GGTase I modification of proteins. Possible formats include, but are not limited to, a bullet point list, a list of frequently asked questions (FAQ) or a chart. Additionally, the information to be imparted can be illustrated in non-textual terms using pictures, graphics, or other symbols.

"Pre-recorded media device" can be, for example, a visual media device, such as a videotape cassette, a DVD (digital video disk), filmstrip, 35 mm movie, or any other visual media device. Alternately, pre-recorded media device can be an interactive software application, such as a CD-ROM (compact disk-read only memory) or floppy disk. Alternately, pre-recorded media device can be, for example, an audio media device, such as a record, audiocassette, or audio compact disk. The information contained on the pre-recorded media device can describe the use of the dosage forms and compounds or liposomes described herein to treat a condition or disease, for example, to treat a cancer involving GGTase I modification of proteins.

A "planner" can be, for example, a weekly, a monthly, a multi-monthly, a yearly, or a multi-yearly planner. The planner can be used as a diary to monitor dosage amounts, to keep track of dosages administered, or to prepare for future events wherein taking a regularly administered dosage form as described herein. Alternately, the planner can be a calendar which will provide a means to monitor when a dosage has been taken and when it has not been taken. This type of planner will be particularly useful for patients having unusual schedules for administering medication to themselves. Additionally, the planner can be useful for the elderly, children, or other patient group who may administer medication to themselves and may become forgetful. One skilled in the art will appreciate the variety of planning tools that would be appropriate for use with compounds and dosage forms described herein.

The kit can also include a container for storing components of the kit. The container can be, for example, a bag, box, envelope or any other container that would be suitable for use with the compounds and dosage forms described herein. Preferably, the container is large enough to accommodate each component and/or any administrative devices that may be accompany the dosage form of the present invention. However, in some cases, it may be desirable to have a smaller container which can be hidden in a patient's pocketbook, briefcase, or pocket.

In some embodiments, the present invention includes a kit comprising a pharmaceutical dosage form described herein. In some embodiments, the kit further comprises printed instructions for its use. In some embodiments, the kit further comprises a printed matter, a pre-recorded media device, or a planner describing the use of the pharmaceutical dosage form of the present invention to treat or prevent a condition which could be aided by taking the compositions disclosed herein.

In some aspects, the present invention provides a method of delivering a pharmaceutical dosage form described herein, to a patient in need thereof, the method comprising:

registering in a computer readable storage medium the identity of a physician permitted to prescribe the pharmaceutical dosage form;

providing the patient with counseling information concerning a risk attendant to the pharmaceutical dosage form;

obtaining informed consent of the patient to receive the pharmaceutical dosage form despite the risk;

registering the patient in the computer readable medium after obtaining the informed consent; and permitting the patient access to the pharmaceutical dosage form.

In some embodiments of this method, the access to the pharmaceutical dosage form is a prescription.

Still other aspects of the present invention include a method of educating a consumer regarding the pharmaceutical dosage forms described herein, the method comprising distributing the oral pharmaceutical dosage form to a consumer with consumer information at a point of sale.

In some embodiments, the consumer information is presented in a format selected from the group consisting of: English language text, a foreign language text, a visual image, a chart, a telephone recording, a website, and access to a live customer service representative. In some embodiments, the consumer information is a direction for use, appropriate age use, indication, contraindication, appropriate dosing, warning, telephone number, or website address.

In some embodiments, the method of educating the consumer further comprises providing professional information to a relevant person in a position to answer a consumer question regarding the pharmaceutical dosage form. In some embodiments, the relevant person is a physician, physician assistant, nurse practitioner, pharmacist, or customer service representative.

In some embodiments, the distributing of the pharmaceutical dosage form is to a location with a pharmacist or a health care provider.

EXAMPLES

Example I

Characterization of Compounds

A. Experimental Procedures

A. Cell Lines and Cell Culture—

NIH3T3 cells were maintained in Dulbecco's modified Eagle's medium (DMEM; Cellgro, Herndon, Va.) supplemented with 10% (v/v) fetal bovine serum (FBS; Hyclone, Logan, Utah), 2% L-glutamine, 1% penicillin, and 1% streptomycin stock solutions (Life Technologies, Gaithersburg, Md.). K562 cells were maintained in RPMI-1640 medium (Cellgro) supplemented with 10% (v/v) FBS and penicillin/streptomycin. PANC-1 cells were maintained in DMEM/F12 medium (Invitrogen, Grand Island, N.Y.) supplemented with 10% (v/v) FBS and penicillin/streptomycin. MCF-7 cells were maintained in Eagle's Minimum Essential Medium (EMEM; Cellgro) supplemented with 10% (v/v) FBS and penicillin/streptomycin.

B. Materials—

[$^3$H]-farnesyl diphosphate (FPP) (21.5 Ci/mmol) and [$^3$H]-geranylgeranyl diphosphate (GGPP) (23.0 Ci/mmol) were purchased from PerkinElmer Life Sciences. BMS-225975 was kindly provided by Dr. Veeraswamy Manne (Bristol-Myers Squibb). GGTI-298 was purchased from Calbiochem (La Jolla, Calif.). Prenyltransferases used are recombinant enzymes. GGTase-I, FTase, RabGGTase, REP-1 and Rab7 were purchased from JENA BIOSCIENCE (Jena, Germany). Other chemicals were obtained from Sigma. The allenoate derived compounds library including P3-E5 and P5-H6 were synthesized as described. Examples of suitable methods for the synthesis of, e.g, P61-A6 and P61-B4 have been described above.

C. In Vitro Enzyme Assays—

GGTase-I and FTase activities were determined by following the incorporation of radiolabeled isoprenoid [$^3$H]-geranylgeranyl or [$^3$H]-farnesyl into substrate proteins. FTase or GGTase-I (50 nM) were used to initiate reactions containing 0.4 µM of [$^3$H]-FPP or 0.5 µM of [$^3$H]-GGPP and 2 µM of MBP-tagged substrates (K-Ras4B for FTase; RhoA for GGTase-I) in 20 µl of buffer {50 mM Tris-HCl (pH 7.5), 10 mM MgCl$_2$, 50 mM ZnCl$_2$ and 5 mM DTT}. Inhibitors were added at the indicated concentrations. The final DMSO concentration was 2.5% for all samples.

Reactions were carried out for 10 min at 30° C. The reaction mixture was spotted onto a filter paper, treated with 10% trichloroacetic acid (TCA) followed by ethanol and acetone washing. The filter was counted using a scintillation counter.

Kinetic assays in which the GGPP concentration was varied employed fixed concentrations of GGTase-I and RhoA, and reactions were carried out for 5 min. Similarly, fixed concentrations of GGTase-I and GGPP were used when the amount of RhoA was varied.

For RabGGTase assays, the reaction contained the following components in 20 µl; 0.625 µl of [$^3$H]-GGPP (0.7 µM), 25 nM RabGGTase, 0.6 µM REP-1, 0.6 µM purified Rab7 or Ypt1 protein, 40 mM HEPES (pH 7.5), 150 mM NaCl, 5 mM DTT, 3 mM MgCl$_2$ and 0.3% CHAPS. Reactions were carried out for 20 min at 37° C. and the products were analyzed as described above for the GGTase-I reaction. Graphing and Michaelis-Menten analysis were performed using Prism versions (GraphPad, San Diego Calif.).

D. Inhibition of Geranylgeranylation in Cells—

The inhibition of GGTase-I catalyzed protein geranylgeranylation was assessed by examining the accumulation of unprenylated Rap1. To measure the level of unprenylated Rapt, cells were cultured in DMEM plus 10% (v/v) FBS overnight, and then DMSO or appropriate inhibitors were added. Incubation was continued for 48 hours. The cells were harvested and lysed in lysis buffer (20 mM Tris-HCl, pH 7.5, 150 mM NaCl, 1 mM EDTA, 1% NP-40 and 1× Protease Inhibitor Cocktail). Whole cell lysates of NIH3T3 cells were electrophoresed on a 12% SDS-PAGE, transferred to nitrocellulose membranes and immunoblotted with the antibody against unprenylated form of Rap1 (Santa Cruz Biotechnology catalog number sc-1482, goat), total-Rap1 (Santa Cruz: sc-65) or actin (Sigma: A4700). Actin was used as a loading control.

The inhibition of Rab geranylgeranylation in cells was examined according to Castellano et al. (2007) *J. Am. Chem. Soc.* 129, 5843-5845. (29). Briefly, whole cell lysates were subjected to 15% SDS-PAGE containing 4M urea followed by immunoblotting with the antibody against Rab5b (Santa Cruz: sc-598) or actin. Subcellular fractionations (FIG. 4) were performed as described by Gomes et al. (30). Briefly, cells were treated with P49-F6 for 48 hours. After osmotic lysis, cell debris were removed by centrifugation at 500×g for 10 min, and the supernatant was subjected to ultracentrifugation at 100,000×g for 60 min. The supernatant of ultracentrifugation was collected as a soluble fraction. The pellet was collected as a membrane fraction. These fractions were subjected to electrophoresis on 10% SDS-PAGE gels followed by immunoblotting with the antibody against Rab5b. RhoGDI (Santa Cruz: sc-360) and Na$^+$/K$^+$ ATPase (Sigma: A276) were used as markers for soluble and membrane fractions, respectively.

E. Cell Viability, Cell Cycle Analysis—

Cell viability was determined by Cell Counting Kit-8 (CCK-8, Dojindo, Kumamoto, Japan) as described previously (Gomes et al. (2003) *Mol. Biol. Cell* 14, 1882-1899). Briefly, cells (5×10$^3$) were plated onto 96-well plates and treated with the appropriate inhibitor as indicated in figure legends. Cell viability was calculated relative to the DMSO control. Cell cycle profile was analyzed by flow cytometry as described previously (Lu et al. (2007) *Small* 3, 1341-1346).

F. Transcriptional Reporter Assays—

For the p21$^{WAF1/CIP1}$ promoter luciferase assay, NIH3T3 cells were transfected with p21$^{WAF1/CIP1}$ promoter-Luc or vector plasmids (Kato-Stankiewicz et al. (2002) *Proc. Natl. Acad. Sci. USA* 99, 14398-14403) (both plasmids are provided by Dr. Genhong Cheng). Cells were treated with GGTI compounds. Promega luciferase assay kit was used according to the manufacturer's protocol.

G. Statistical Analysis—

Statistical significance of difference was determined using the unpaired Student's t-test. P value <0.05 was considered statistically significant.

B. Results of In Vitro Studies

Cellular Activity of Compounds, Including P61-A6 and P61-B6

P61-A6 and P61-B6, showed good potency with IC50 of 2.2 µM and 5.0 µM to inhibit proliferation of K562 cells, respectively. Comparison of inhibitory activity of P5-H6 and P61-A6 on a pancreatic cancer cell line PANC-1 and Jurkat cells is shown in FIG. 1B.

The potency of these compounds to inhibit cell proliferation correlates with their increased ability to inhibit protein geranylgeranylation inside the cell. Results illustrating this correlation using P5-H6 and P61-A6 are shown in FIG. 1C. In this experiment, the inhibition of protein geranylgeranylation can be evaluated using an antibody that specifically detects unprenylated Rap1. Treatment with P5-H6 or P61-A6 led to the appearance of the unprocessed Rap 1 band in a dose dependent manner. The appearance of the Rap1 band is observed at 2.5 µM concentration with P61-A6, while this is not seen with P5-H6, reflecting improvement in the potency of P61-A6 to inhibit protein geranylgeranylation.

In contrast to its effects on GGTase-I, P61-A6 did not inhibit protein farnesylation. This was examined by using a farnesylated protein H-Ras. While farnesyltransferase inhibitor (FTI) (BMS-225975) slowed the mobility of H-Ras protein on a SDS polyacrylamide gel, no such mobility shift was observed with P61-A6 or another GGTI compound, GGTI-298. Similarly, P61-A6 did not inhibit geranylgeranylation of Rab5b, as a slow migrating band representing that of unmodified Rab5b was detected only after the treatment with RabGGTase inhibitors (P49-F6) and not with P61-A6 (FIG. 1E).

GGTI Compounds Inhibit Proliferation of Various Human Cancer Cell Lines and Cause G$_1$ Cell Cycle Arrest.

As shown in Table 4, inhibition of cellular proliferation was observed in a variety of human cancer cell lines. These results indicate that a broad range of human cancer cell lines can be inhibited using the GGTI compounds described herein.

TABLE 4

Potencies of GGTIs toward human cell lines

|  |  | P61-A6 | P61-B6 |
| --- | --- | --- | --- |
| Jurkat | Blood | 2.9 | 1.3 |
| SE-Mk2 | Blood | 6.4 | 14.1 |
| PANC-1 | Pancreas | 5.2 | 12.6 |
| MiaPaCa2 | Pancreas | 4.7 | 13.9 |
| AsPc-1 | Pancreas | 11.7 | >20.0 |
| Capan-2 | Pancreas | 11.5 | 11.1 |
| CFpac-1 | Pancreas | 6.3 | 8.1 |
| HPAC | Pancreas | 3.9 | 11.7 |
| MDA-MB-231 | Breast | 8.7 | 12.5 |
| BT474 | Breast | 8.5 | 11.6 |
| MCF-7 | Breast | 4.5 | 6.4 |

Cancer cells were treated with the indicated GGTIs for 3 days (Jurkat, PANC-1, MiaPaCa2, Capan-2, CFpac-1, HPAC, MDA-MB-231 and BT474) or 6 days (SE-MK2, AsPc-1 and MCF-7), and cell number was counted using CCK-8 and compared with vehicle (DMSO) treated cells. Values are the IC50 (µM) for at least two separate experiments.

Figure 2:
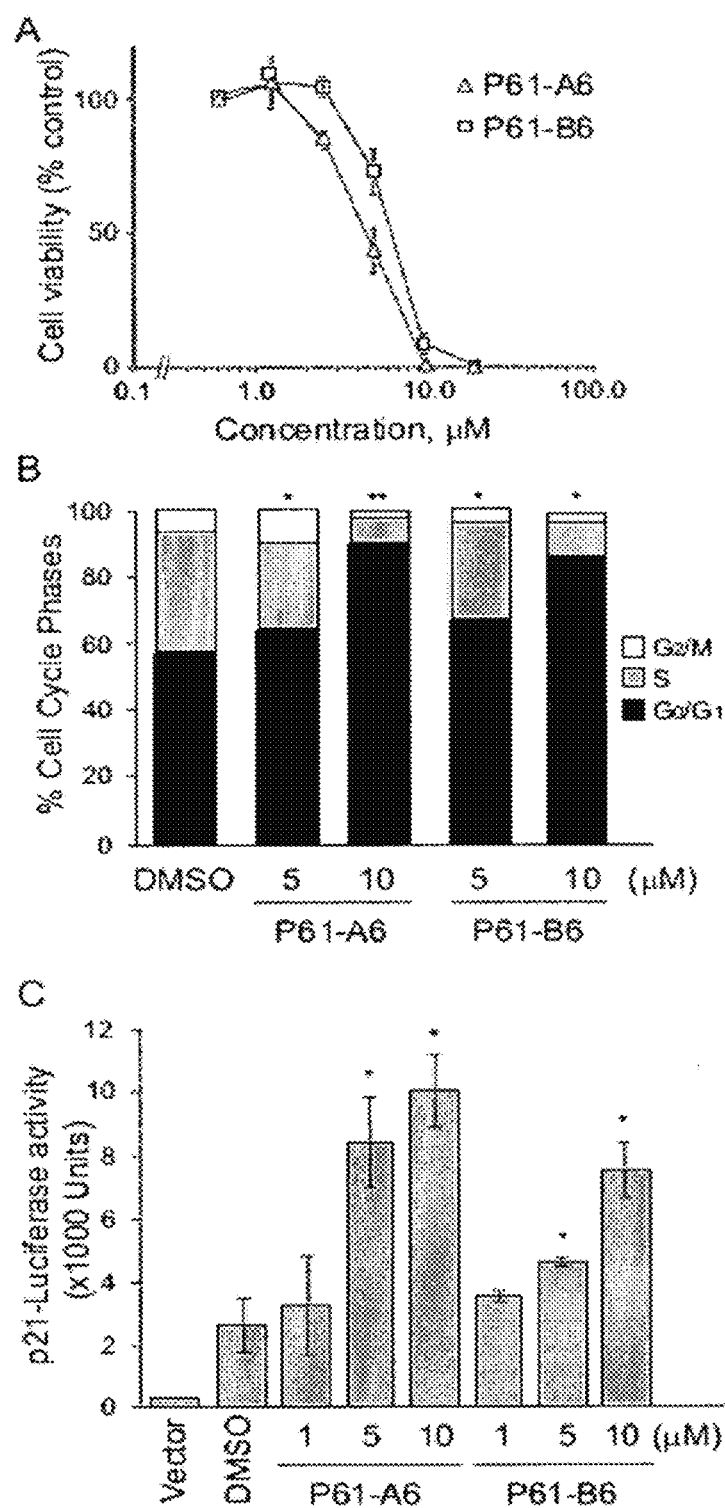
FIG. 2 shows the effects of P61-A6 or P61-B6 on cell proliferation and cell cycle in MCF-7 cells. (A) shows the inhibition of proliferation of MCF-7 by P61-A6 and P61-B6. MCF-7 cells were treated with P61-A6, P61-B6 or DMSO for 72 hours. Cell viability relative to the DMSO control (100% value) is plotted. (B) MCF-7 cells were treated with indicated concentrations (µM) of P61-A6, P61-B6 or DMSO for 48 hours. Cell cycle profiles were monitored by flow cytometry. Percentages of cells in each phase of the cell cycle are indicated by different shades. (C) NIH3T3 cells were transfected with $p21^{CIP1/WAF1}$-luciferase or empty vector. Cells were treated with P61-A6 or P61-B6 compound at indicated concentrations or with DMSO for 48 hours and luciferase assay was performed. Data represent the mean+/−S.D. of two measurements from two independent experiments. *, P<0.05; **, P<0.005 compared with the value for DMSO.
Figure 3:
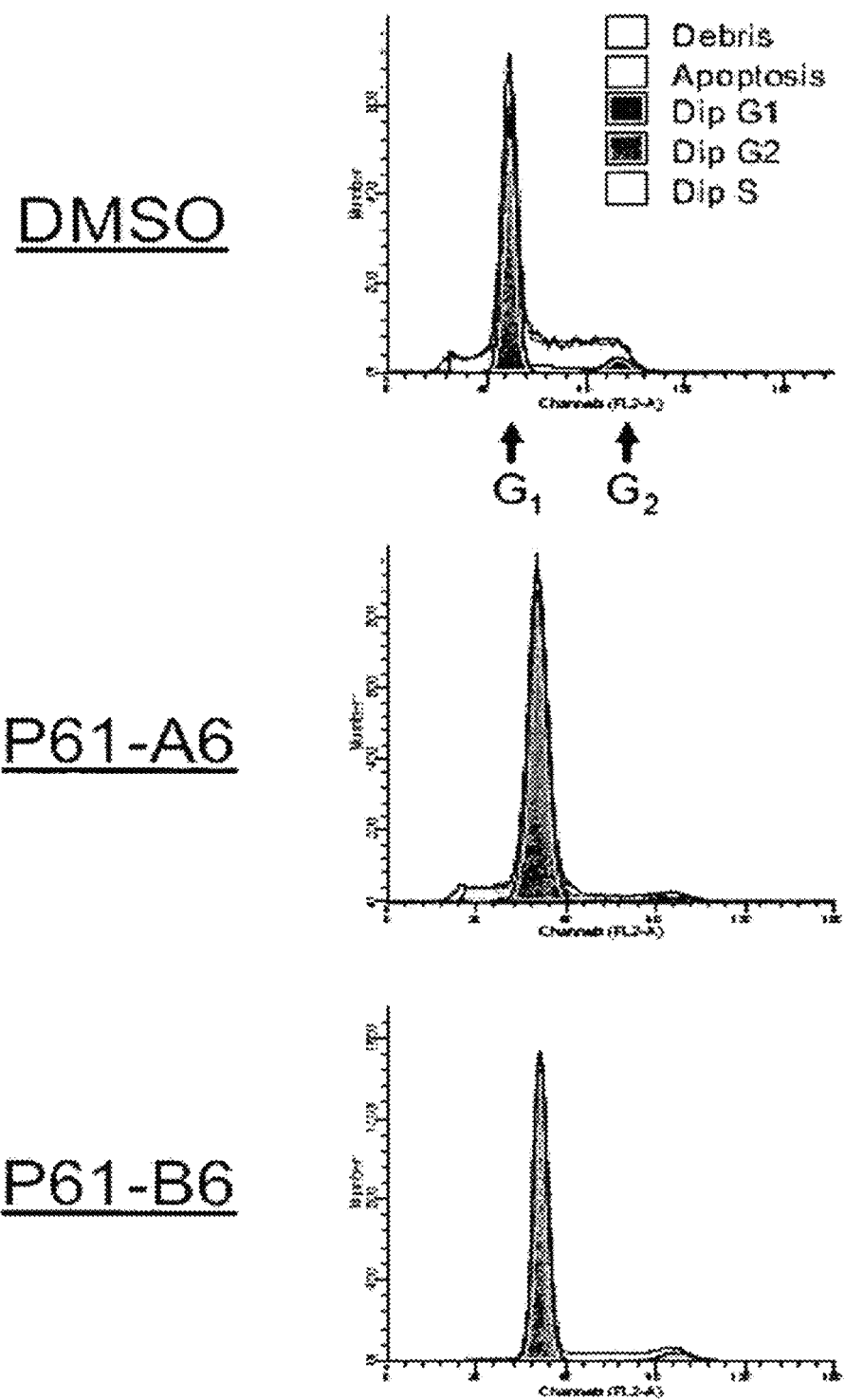
FIG. 3 shows primary FACS data. MCF-7 cells were treated with 10 µM of P61-A6, P61-B6 or DMSO for 48 hours. Data shown here are representative of two independent experiments for each treatment.

While not wishing to be bound to a single theory, it is suggested that the inhibition of cellular proliferation by GGTI may be due to the inhibition of cell cycle progression. Treatment of a breast cancer cell line (MCF-7) with P61-A6 or P61-B6 caused dose-dependent inhibition of proliferation. This is associated with a significant dose-dependent enrichment of G$_1$ phase cells, while the percentage of S-phase cells decreased (FIG. 2B, FIG. 3). Similar $G_1$ enrichment was observed with leukemic cell line, Jurkat, two pancreatic cancer cell lines, PANC-1 and MiaPaCa2, as well as with another breast cancer cell line MDA-MB-231 (Table 5).

TABLE 5

Effects of GGTIs on cell cycle phase distribution in cancer cells

| Cell line | Tissue | Percent $G_0/G_1$ | | P value | Percent $G_2/M$ | |
|---|---|---|---|---|---|---|
| | | DMSO | P61-A6 | | DMSO | P61-A6 |
| Jurkat | Blood | 46.92 | 57.87 | <0.05 | 11.80 | 11.60 |
| PANC-1 | Pancreas | 42.08 | 54.13 | <0.005 | 24.21 | 19.81 |
| MiaPaCa2 | Pancreas | 77.85 | 87.98 | <0.05 | 14.12 | 10.81 |
| MDA-MB-231 | Breast | 73.78 | 85.16 | <0.05 | 7.74 | 5.15 |

NOTE:
Cancer cells were treated with the P61-A6 (10 μM) for 48 hours, and cell cycle distribution was determined by flow cytometry as described under "Experimental Procedures". Data are representative of at least two independent experiments.

Another mechanism through which GGTI can effect cell cycle progression is to inhibit RhoA which negatively regulates expression of a Cdk inhibitor $p21^{CIP1/WAF1}$. To investigate whether the GGTI compounds described herein can induce $p21^{CIP1/WAF1}$ expression, luciferase transcriptional activation from the $p21^{CIP1/WAF1}$ promoter was measured. Transient expression systems with NIH3T3 cells were used to examine the ability of P61-A6 to induce $p21^{CIP1/WAF1}$-luciferase expression. P61-A6 induced significant (4-fold) inductions of luciferase activity versus DMSO in a dose dependence manner (FIG. 2C).

Discussion

The above experiments illustrate the identification of novel small molecule inhibitors of GGTase-I from the diversity library of allenoate-derived compounds. The compounds of the invention are non-peptidomimetic inhibitors that compete with the substrate protein. Specific inhibition of protein geranylgeranylation but not protein farnesylation was established with the purified enzymes as well as with treated cells. Other non-peptidomimetic GGTI compounds have been reported. However, a surprising low concentration of 2-20 μM of the compounds described herein can be used to exert cellular activity with tissue culture cells.

The improvement of the cellular activity of our GGTI compound can be correlated with the increase in the ability to inhibit protein geranylgeranylation, as detected by the appearance of unprenylated Rap1 protein. On the other hand, the modification did not improve potency of these compounds to inhibit GGTase-I enzyme. Therefore, without wishing to be bound to any particular mechanism, it is suggested that the improvement of cellular activity may reflect increased cellular uptake or stability of the compound.

The GGTI compounds described herein exhibit inhibition of proliferation of human cancer cell lines including leukemic, pancreatic cancer and breast cancer cell lines. One of the hallmarks of GGTI is that this class of inhibitors causes cell cycle arrest at the $G_1$ phase. These inhibitors exhibit significant $G_1$ arrest with the human cancer cell lines examined (FIG. 2B, Table 5). In particular, dramatic $G_1$ arrest is observed with a breast cancer cell line MCF-7. In addition, our GGTI compounds induce $p21^{CIP1/WAF1}$ expression, as observed by using a luciferase reporter assay. These results indicate that our GGTI inhibits RhoA which acts as a negative regulator of $p21^{CIP1/WAF1}$ expression.

C. Inhibition of Tumor Growth with the Compounds In Vivo.

Xenograft tumor experiments have shown that GGTI's can inhibit PANC-1 tumor growth in mice. Seven SCID mice (six weeks old) received a subcutaneous implantation of 5 million PANC-1 cells. The mice were supplied with food and water for 14 days before treatment was started. The treatment group received 160 uM GGTI (p61A6) in 0.25 ml 0.9% NaCl while the control group received 0.25 ml 0.9% NaCl. Each dosage was injected 3 times per week. These dosage were designed to administer p61A6 at approximately 1.16 mg/kg of body weight. Also, since the mouse has about 2 ml blood, the final concentration of p61A6 in vivo was approximately 20 uM. The final DMSO concentration in the control group was approximately 0.8%.

Figure 4:
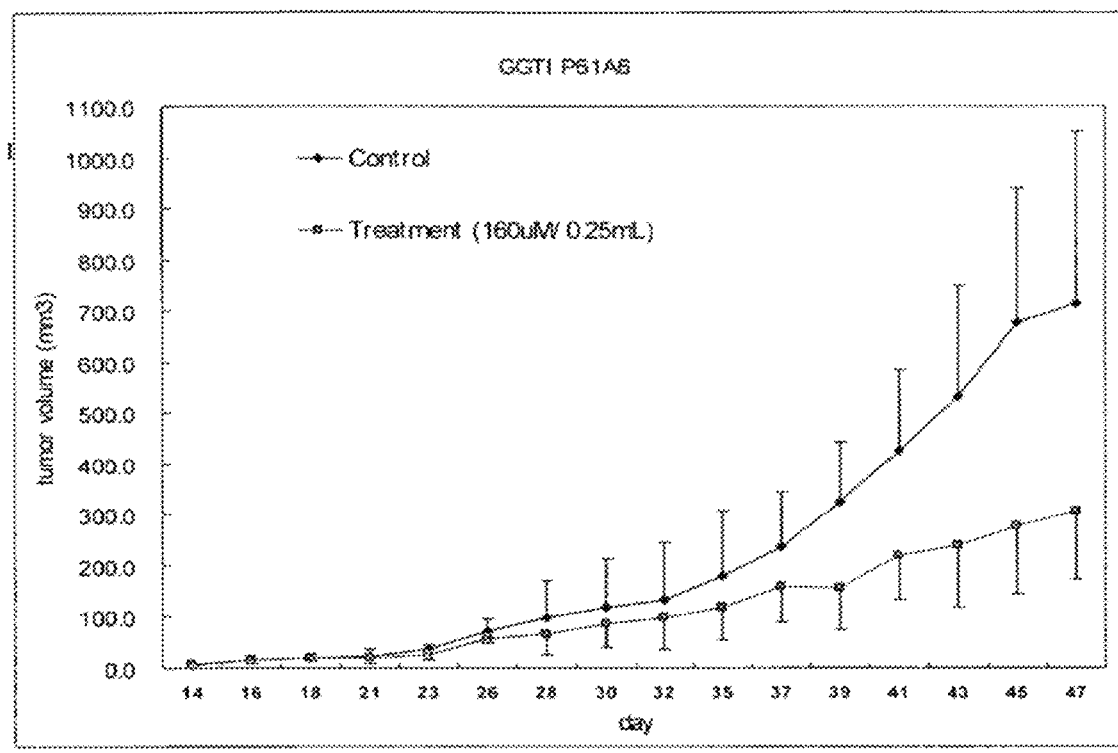
FIG. 4 shows that P61A6 inhibits PANC-1 xenograft tumor growth in SCID mice.
Figure 5:
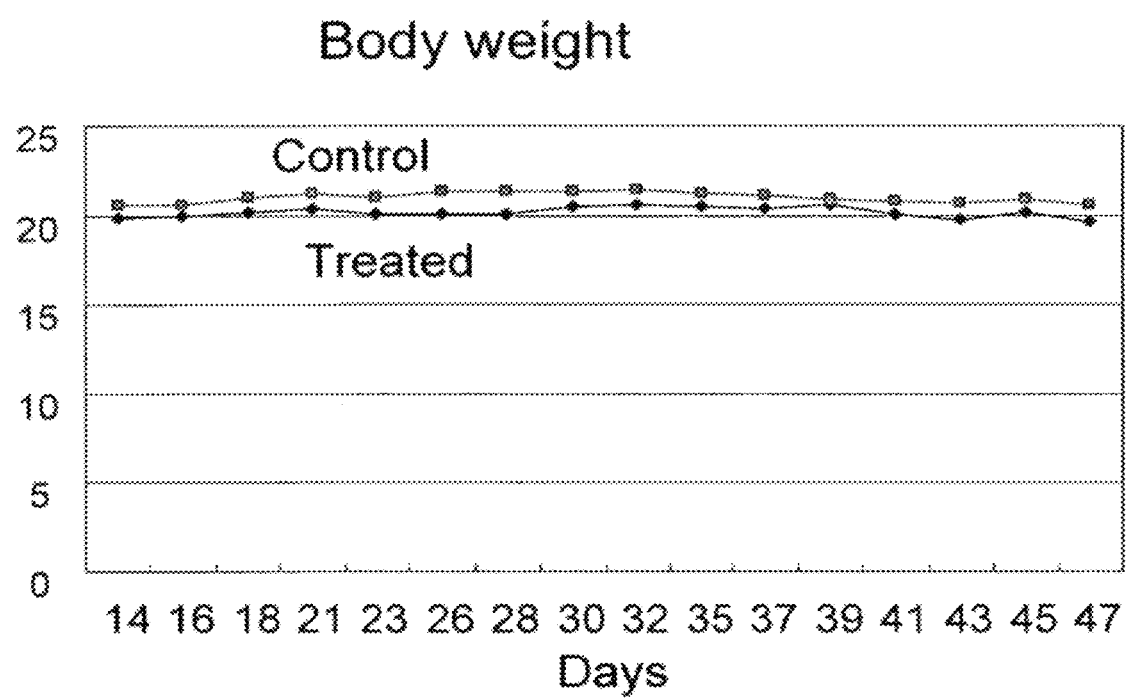
FIG. 5 shows an examination of mouse body weight indicating that the GGTI treatment did not cause adverse effects.

Results from the test are shown in FIGS. 4 and 5 and Table 6 below. These results indicate that GGTI P61A6 inhibits PANC-1 xenograft tumor growth in SCID mice. FIG. 5 and Table 6 show examinations of body weight as well as hematological and biochemical examinations indicating that the GGTI treatment did not cause adverse effects.

TABLE 6

| | GGTI treated 4 | control 1 |
|---|---|---|
| ALB | N | N |
| ALT (7-227) | N | N |
| AST (37-329) | N | N |
| BUN | N | N |
| CREAT | N | N |
| CHOL | N | N |
| CK | N | N |
| ALP | N | N |
| GLU | N | N |
| CA | N | N |
| RBC | N | N |
| WBC | N | N |
| NE | N | N |
| LY | N | N |
| PLT | N | N |

Additional xenograft tumor experiments have shown that GGTI's can inhibit PANC-1 tumor growth in mice and reduce the size of the tumor. Six SCID mice (six weeks old) received a subcutaneous implantation of 3 million PANC-1 cells. The mice were supplied with food and water for 14 days before treatment began. The mice were divided into the following treatment groups (all non-control groups administered P61-A6 at the dose listed): (1) control: 0.25 ml 0.9% Nacl; (2) treatment group 1: 1.16 mg/kg of body weight in 0.25 ml 0.9% Nacl, 1/week, i.p. (20 uM); (3) treatment group 2: 1.16 mg/kg of body weight in 0.25 ml 0.9% Nacl, 6/week, i.p. (20 uM); (4) treatment group 3: 0.58 mg/kg of body weight in 0.25 ml 0.9% Nacl, 3/week, i.p. (10 uM); and (5) treatment group 5: 0.29 mg/kg of body weight in 0.25 ml 0.9% Nacl, 3/week, i.p. (5 uM). Every two weeks each mouse's body weight and tumor volume was measured.

Figure 6:
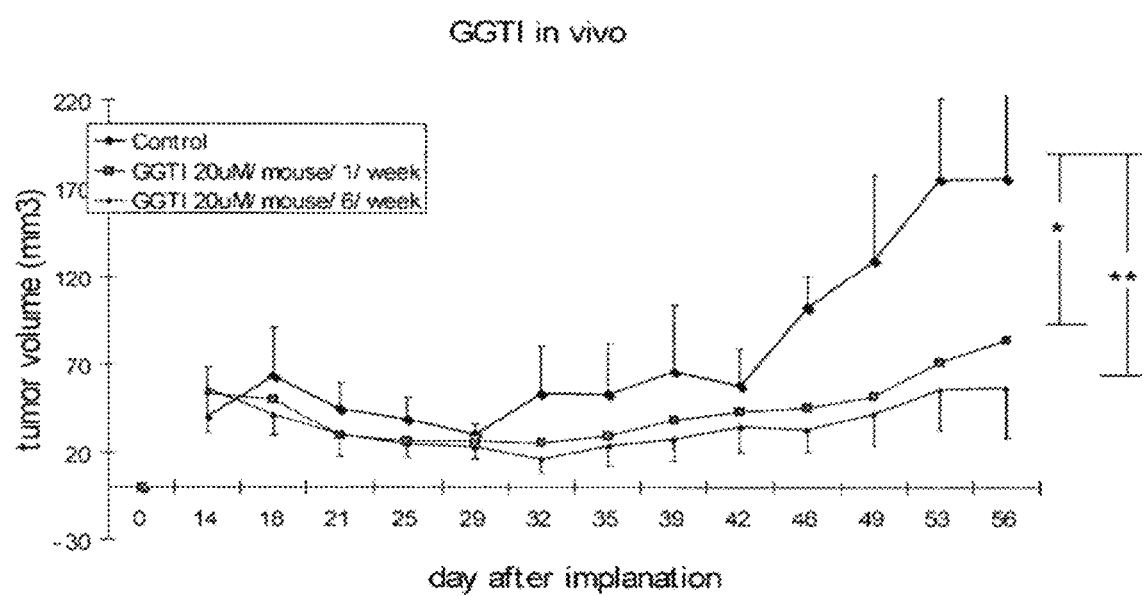
FIG. 6 shows that P61A6 inhibits PANC-1 xenograft tumor growth in SCID mice.
Figure 7:
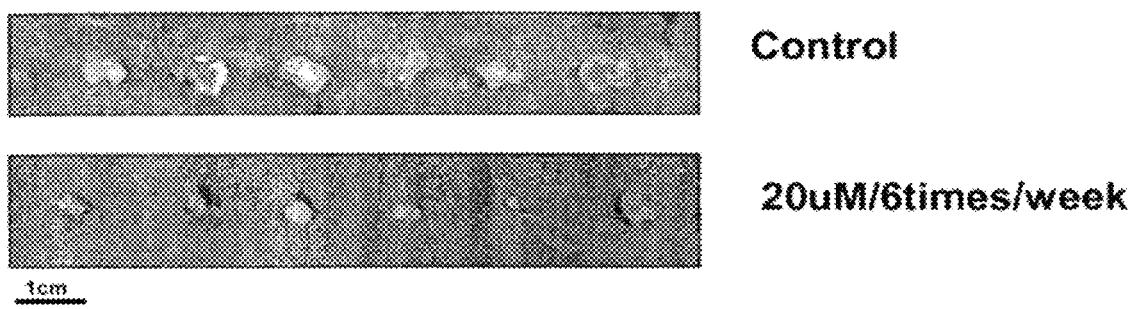
FIG. 7 shows that the PANC-1 cell tumor size was reduced by administering P61A6 six times per week.
Figure 8:
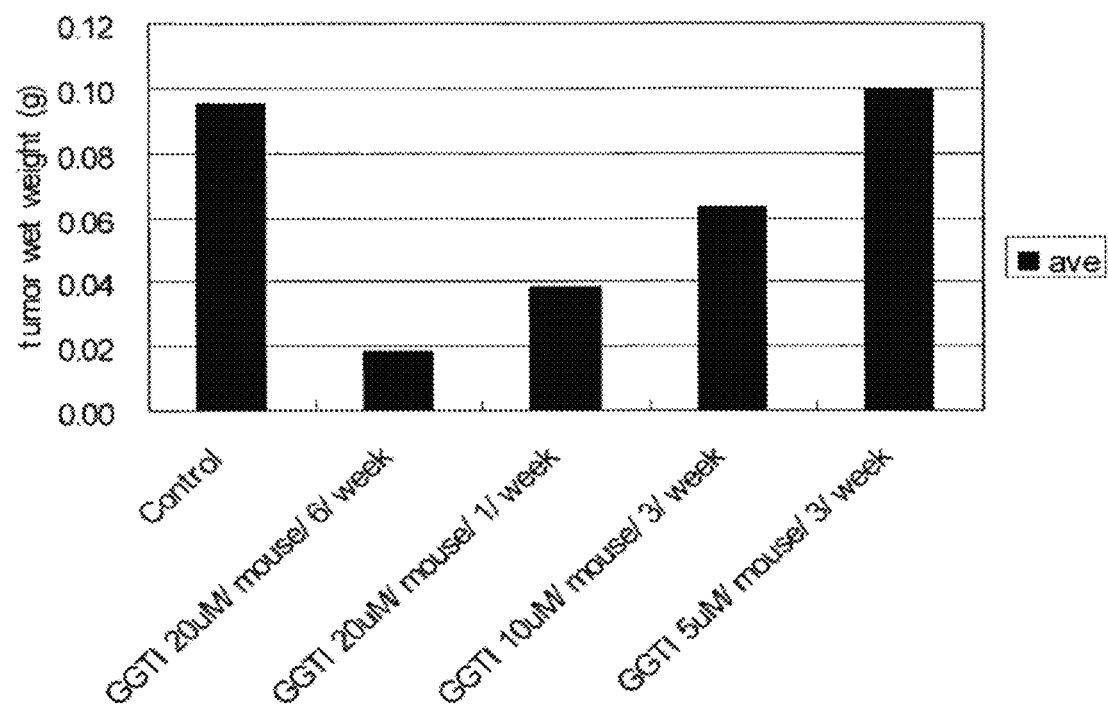
FIG. 8 shows dose dependent inhibition of a xenograft tumor by P61A6.
Figure 9:
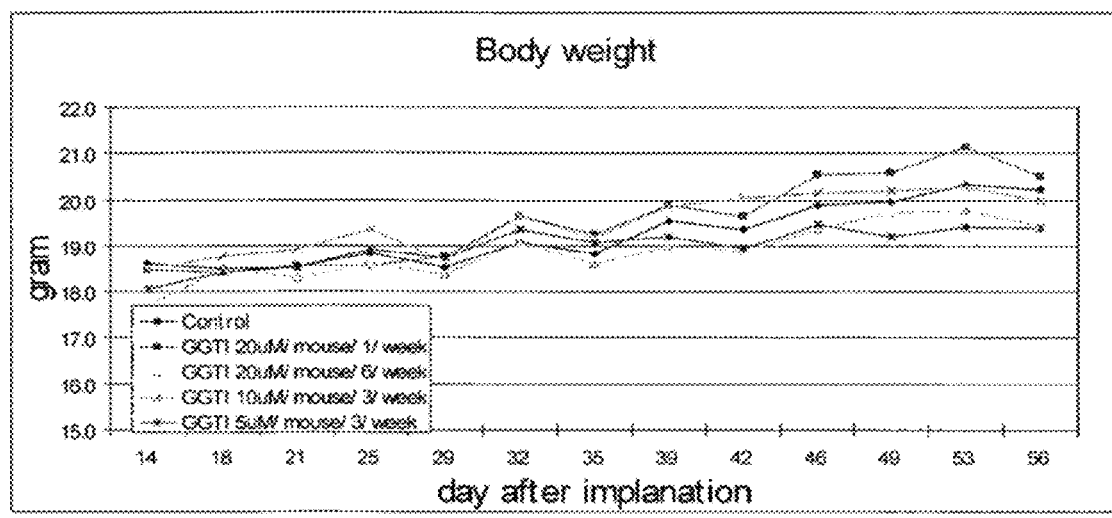
FIG. 9 shows that the administration of P61A6 did not significantly effect mouse body weight.
Figure 10:
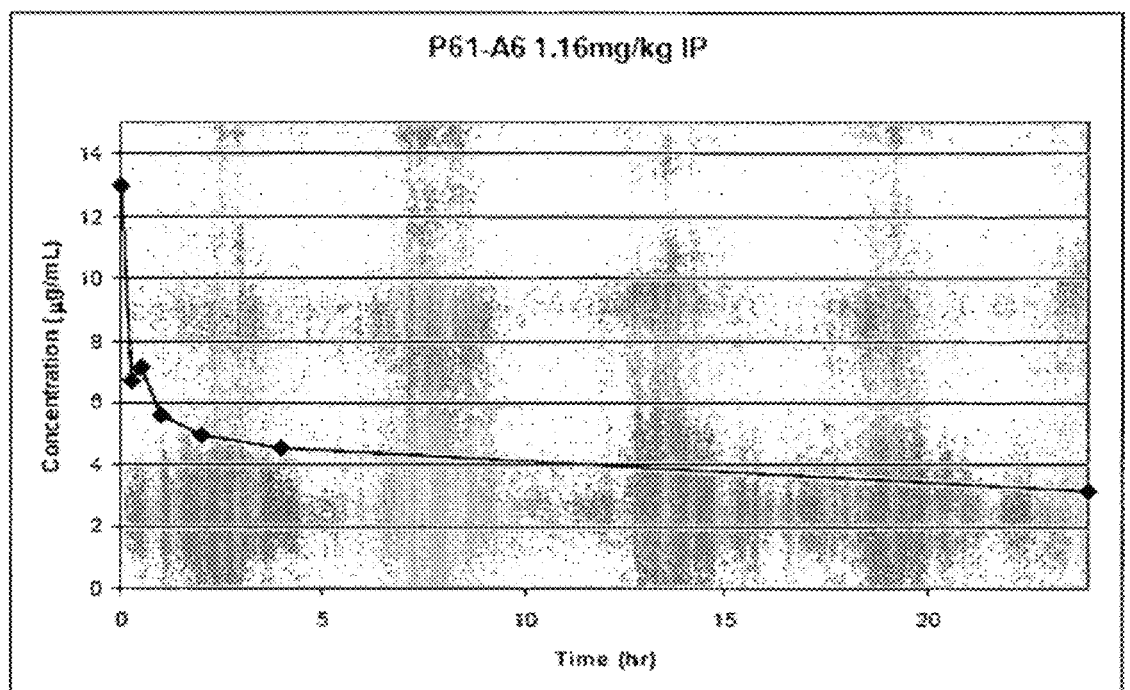
FIG. 10 shows the serum levels of P61A6 over time.

As shown in FIG. 6, almost complete inhibition of PANC-1 tumor growth was obtained by administering GGTI P61-A6 six times per week. Surprisingly, similar inhibition was observed administering GGTI P61-A6 once a week. This may be due to slow metabolism of the compound. Table 7 illustrates that GGTI P61-A6 was found to have a half life of 16.9 hours. Thus, in some embodiments, the compositions of the invention can be administered is a dosage regimen that is highly convenient, e.g., once weekly instead of daily. The compositions of the present invention can be administered every 1, 2, 3, 4, 5, 6, or 7 days, or may be administered otherwise.

TABLE 7

| Parameter | IP |
|---|---|
| Dose | 1.16 mg/kg |
| $C_{max}$ | 13 µg/ml (22.4 µM) |
| $AUC_{0-4\,h}$ | 22.2 µg * hr/ml |
| Clearance | 1.04 ml/hr |
| Half-life | 16.9 hr |

Example II

Preparation and Characterization of Liposomes

A. Materials and Methods
Synthesis of Basic Liposomes and Transferrin-Conjugated (Trasnferrin-PEG) Liposomes Cationic charged liposomes are prepared by incorporating stearylamine as a charged lipid into the formulation as described. Nonionic and anionic charged liposomes are prepared by altering the molarity of DPPG as the charged lipid. For the preparation of an aqueous solution of the drug in water, it is necessary to determine the concentrations of liposomes according to the molarity of the DPPG as the charged lipid. This cationic liposome contains not only 0,0'-ditetradecanoyl-N-(α-trimethylammonioacetyl) diethanolamine chloride (DC-6-14) as a cationic lipid, but also DOPE and cholesterol, and this confers the characteristics of efficient transfection activity and expression.

Tf-PEG liposomes were prepared by coupling human iron-saturated Tf to the COOH site of PEG liposomes as described. Average sizes of these liposomes were about 180-200 nm and there were no significant differences in average size between bare liposomes, PEG liposomes and Tf liposomes.

Design and Synthesis of pH-Sensitive Polymer-Liposomes pH-sensitive liposomes were specially designed so that they release their contents at a pH of about 6 or lower. This was accomplished by altering the ratio of two lipids—Palmitoyl oleoyl PC (POPC) and DSPE-PG8MG. POPC is a synthetic compound rather than a naturally occurring compound, which allows for consistency among different lots. In addition, POPC is less prone to oxidation than other lipids, such as EYPC. The lyophilized liposomes were prepared by adding sucrose during the lyophilization step to function as a cryoprotectant. In embodiments of the invention, the molar ratio of these two lipids is about 85/15, and the liposomes release agents encapsulated therein at a pH of about 6 or lower.

pH-sensitive polymer-liposomes were synthesized by reacting DSPE-PG8G with acid anhydrides, such as 3-methylglutaric anhydride and 1,2-cyclohexanedicarboxylic anhydride. Briefly, after DSPE-PG8G (2.0 g, 1.38 mmol) was dissolved in toluene at 40° C., 3-methylglutaric anhydride (2.39 g, 18.7 mmol) and N-methylmorpholine (2.08 mL, 18.9 mmol) were added. The mixed solution was then stirred at 40° C. for 5 h. 200 mL of Acetonitrile was then added, and the mixture was cooled on ice to precipitate crystals. The supernatant was removed, and the crystals were washed twice with acetonitrile (200 mL) and dried to obtain MGluPG-PE (1.9 g). The composition of MGluPG-PE was estimated by measuring the integration ratio of the peak of methyl groups at 1.06 ppm to the peak of terminal methyl groups of stearoyl groups with the 1H NMR spectrum. For synthesizing CHexPG-PE, DSPE-PG8G (3.0 g, 2.06 mmol) was dissolved in toluene (70 mL) at 50° C., and 1,2-cyclohexanedicarboxylic anhydride (8.62 g, 55.9 mmol) and sodium acetate (4.7 g 55.9 mmol) were then added. The mixture was stirred at 50° C. for 6 h. The reaction mixture was diluted with chloroform (300 mL) and sodium acetate was removed by filtration. The reaction mixture was concentrated by evaporation and then dissolved in chloroform (100 mL). Acetonitrile (300 mL) was added to recover precipitate. The precipitate was then washed with acetonitrile (300 mL) twice and dried with vacuum.

GGTI Compounds

The allenoate-derived compound library was synthesized as described above and in PCT/US2008/009106. A 20 mM stock solution of GGTI P61A6 in DMSO was kept at −20° C. until use.

Drug-Loaded Liposome Preparation

Figure 11:
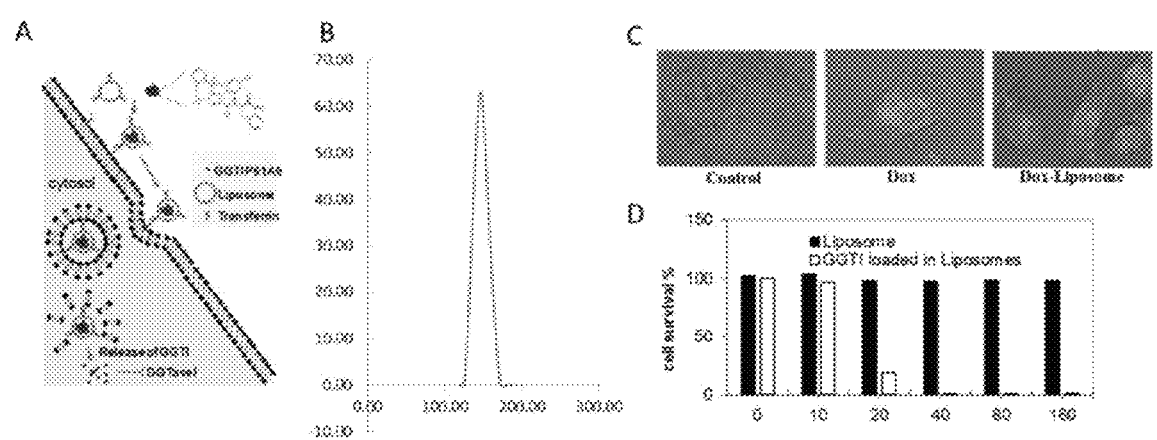
FIG. 11 shows (A) a cartoon of a transferrin-conjugated liposome; (B) size distribution of GGTI loaded liposomes; (C) transport of liposomes into cancer cells; (D) efficacy of GGTI delivered into cells.

A small aliquot (400 µL) of a concentrated solution of GGTI (or, in some cases, Doxorubicin) dissolved in 10% ethanol was mixed with a dry thin membrane of a mixture (7 mg) of liposomes, and the mixture was rotated at 4 C for 15 min followed by sonication for 2 min using a bath-type sonicator. The liposome suspension was extruded through a polycarbonate membrane with a pore size of 100 nm. The liposome suspension was then applied to a Sepharose 4B column to remove free drugs that were not loaded into liposomes from the drug-loaded liposomes. Then 40 ul of liposomes encapsulating GGTI were mixed with 960 ul of Triton X-100 (final concentration: 0.1%) to release the drug from liposomes. The mixtures were then centrifuged through Amicon Ultra-4 to collect free drugs. The elution was measured for concentration of GGTI with HPLC against a standard sample of various concentrations of GGTI. The loading capacity of GGTI into liposomes is approximately 64.5% of total. A DLS study showed that the average size of GGTI-loaded liposomes is approximately 150 nm in diameter (FIG. 11B). There were no significant differences in average size between bare liposomes, PEG liposomes and Tf liposomes.

Loading of pH-sensitive liposomes: By extensive experimentation, it was found that high levels of loading of the pH-sensitive liposomes can be obtained. First, it was found that DMSO used for suspending GGTI interferes with liposome loading as it destroys the liposome. Diluting in buffer was attempted as another loading method, but the GGTI came out of solution. After testing a large number of solvents, it was found that ethanol can be used to dilute GGTI so that DMSO concentration is 10%. Under this condition, GGTI does not come out of solution. Using these conditions, GGTI was loaded into the liposomes and then liposomal GGTI was purified using column chromatography. About 60% of GGTI was shown to be loaded.

Drug Release from Liposomes

Release of drugs from liposomes was measured with High-performance liquid chromatography (HPLC). 40 µl of liposomes encapsulating GGTI were added to 960 µl of PBS buffer with varying pH values, and then mixed at 37 C for 15 min. Triton X-100 was used as a control solution because Triton X-100 can break down the liposomes (final concentration: 0.1%). The mixtures were added to the inner tubes of ultrafilter Amicon Ultra-4 (MWCO=10 kDa, Millipore), centrifuged at 10,000×g for 10 min at room temperature. The elutions were subjected to HPLC to measure the concentration of released GGTI (Waters Micromass LCT Premier Mass Spectrometer).

Cell Culture

The human breast cancer cell line, MCF-7, obtained from the American Type Culture Collection, was maintained in DMEM supplemented with 10% FCS (Sigma), 2% L-glutamine, 1% penicillin, and 1% streptomycin. The medium was routinely changed every 3 days, and the cells were separated by trypsinization before reaching confluency.

Intracellular Behavior of Liposomes

Pyranine-loaded liposomes were prepared as described above. MCF-7 cells ($3\times10^5$ cells) were cultured overnight in an 8 wells glass cell culture chamber. Liposome suspensions were added to the cells and incubated for 4 h at 37° C. After the incubation, the cells were washed with PBS two times and observed with a fluorescent microscope (Carl Zeiss).

Cell Death Assay

The cytotoxicity assay was performed by using a cell-counting kit from Dojindo Molecular Technologies, Inc. Cancer cells were seeded in 96-well plates (5000 cells well-1) and incubated in fresh culture medium at 37° C. in a 5% CO2/95% air atmosphere for 24 h. The cells were then washed with PBS and the medium was changed to a fresh medium containing GGTI-loaded liposomes or empty liposomes as control at the indicated concentrations. After 24 h, the cells were washed with PBS to remove liposomes that were not taken up by the cells, and the cells were then incubated in fresh medium for an additional 48 h. The cells were washed with PBS and incubated in DMEM with 10% WST-8 solution for another 2 h. The absorbance of each well was measured at 450 nm with a plate reader. Since the absorbance is proportional to the number of viable cells in the medium, the viable cell number was determined by using a previously prepared calibration curve (Dojindo Co.).

Western Blot Analysis

Cells were treated with GGTI-liposomes, empty liposomes, or GGTI for 24 h, harvested, and lysed in lysis buffer (1% Triton X-100, 150 mM NaCl, 20 mM Tris-HCl at pH 7.5, 1 mM EDTA, and 1× protease inhibitor mixture). Proteins were separated by gel electrophoresis on a polyacrylamide gel containing SDS and then transferred to nitrocellulose membranes. The membranes were blocked with Tris-buffered saline (TBS) containing 5% (w/v) skimmed milk. After washing with TBS containing 0.1% Tween 20 (Sigma), the membranes were incubated overnight at room temperature with first antibody (unprenylated form of RapI) diluted with TBS. After washing, the membranes were incubated for 2 h at room temperature with the second antibody (Santa Cruz Biotechnology, CA). Bands were detected with an ECL system (Amersham Pharmacia Biotech K.K., UK).

B. Results

1. Basic Liposome-GGTI

To examine the intracellular drug release ability of liposomes, an anticancer drug Doxurubicin was loaded into liposomes, since doxorubicin emits strong red fluorescence under UV excitation. The liposome loading capacity of doxorubicin is similar to that of GGTI. After centrifugation through a Sepharose 4B column to remove free drugs, a homogeneous suspension of the Doxrubicin-loaded liposomes was added to MCF-7 cells that were cultured in an 8 well glass chamber. As a control, a suspension of the same concentration of liposomes in water, or a Doxrubicin solution was added to the cells. 6 hours after incubation, the cells were washed and examined with fluorescence microscopy to image the distribution of CPT in cancer cells. The cells treated with Doxrubicin showed strong red fluorescence (FIG. 11C) after 3 h of incubation in the cytosol, and a part was seen in the nuclei, while those that were treated with liposomes remained non-fluorescent. Cells treated with Doxrubicin-loaded lipsosomes showed strong red fluorescence. This observation indicated that liposomes were able to transport and deliver doxorubicin into cancer cells.

As noted above, one advantage of using nanoparticles is that nanoparticles are able to deliver a drug specifically to a tumor by the enhanced permeability and retention effect (EPR effect), thereby avoiding undesirable systemic chemotoxicity. Since the results above showed that basic liposomes could effectively deliver chemodrugs into cancer cells, the efficacy of GGTI delivered into cells was examined. As shown in FIG. 11D, liposomes without GGTI are not cytotoxic to the cells. However, growth inhibition of MiaPaca-2 cells was observed with GTI-loaded basic liposomes at concentrations starting from 20 μg mL-1, suggesting that liposomes delivered the drugs into cells, and caused cell proliferation inhibition.

2. Transferrin-Conjugated Liposomes-GGTI

Figure 12:
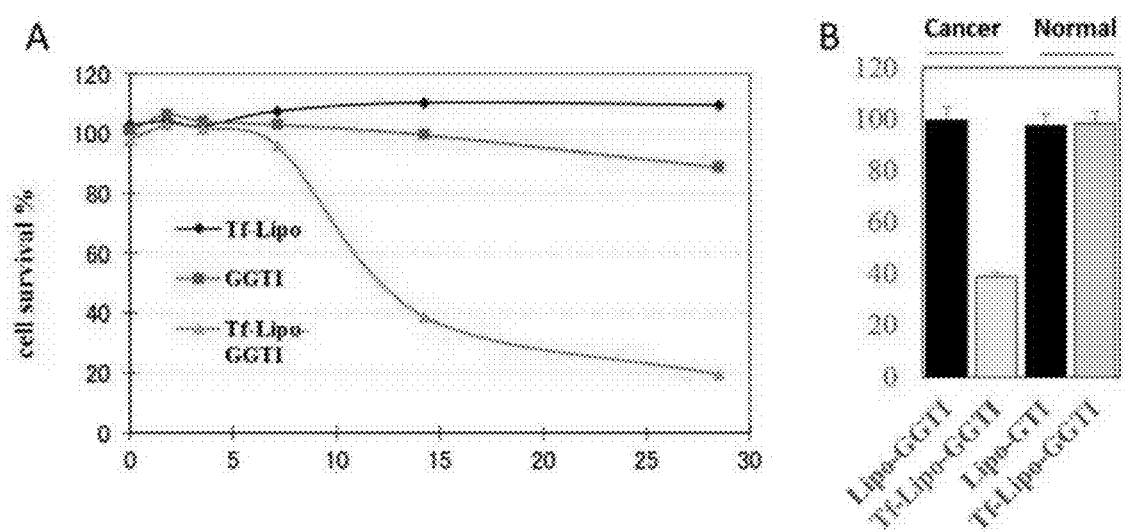
FIG. 12 shows (A) toxicity of Tf-Lipo-GGTI on cancer cells, (B) lack of toxicity of Tf-Lipo-GGTI on normal cells.

In addition to the above mentioned enhanced permeability and retention effect when using liposomes for cancer therapy, attachment of a cancer-targeting moiety or ligand to the lipid nanoparticles results in precise delivery of encapsulated drugs to the tumor, further decreasing systemic side effects. Therefore, we conjugated transferrin on the surface of liposomes. The protein transferrin, which interacts with the upregulated transferrin receptor on cancer cell plasma membranes, was shown to be able to target the nanoparticles to cancers. The enhancement in cell killing of the Tf-Liposome loaded with GGTI is demonstrated through cell proliferation assays. Liposomes without GGTI are not cytotoxic as shown in FIG. 12A. However, growth inhibition of MiaPaca-2 cells was observed with GGTI-loaded basic liposomes (FIG. 11D) at concentrations higher than 20 μg mL-1. By comparison, there was a large increase in the cytotoxicity of Tf-modified GGTI-loaded liposomes, starting from a concentration of 10 μg mL-1 to cancer cells compared to that of untargeted GGTI-loaded liposomes, which correlated with the enhanced liposome intracellular uptake. When treating the cells with 15 ug/ml GGTI-loaded basic liposomes, no cytotoxicity was observed on either cancer cell MiaPaca-2 or normal human fibroblast cells HFF (FIG. 12B). However, significant cell proliferation inhibition was observed on MiaPaca-2 pancreatic cancer cells with Tf-modified liposomes loaded with GGTI, while no change was shown with normal cell line (FIG. 12B). These results indicate that the increased liposome uptake, caused by the Tf surface modification, delivers more drug to cancer cells that overexpress the Tf receptor and is therefore more cytotoxic to these cells than to normal cells.

3. pH-Sensitive Polymer Liposomes—GGTI

P61-A6 was loaded into pH-sensitive polymer liposomes as described above.

Cellular Uptake and Lysosomal Localization

Figure 14:
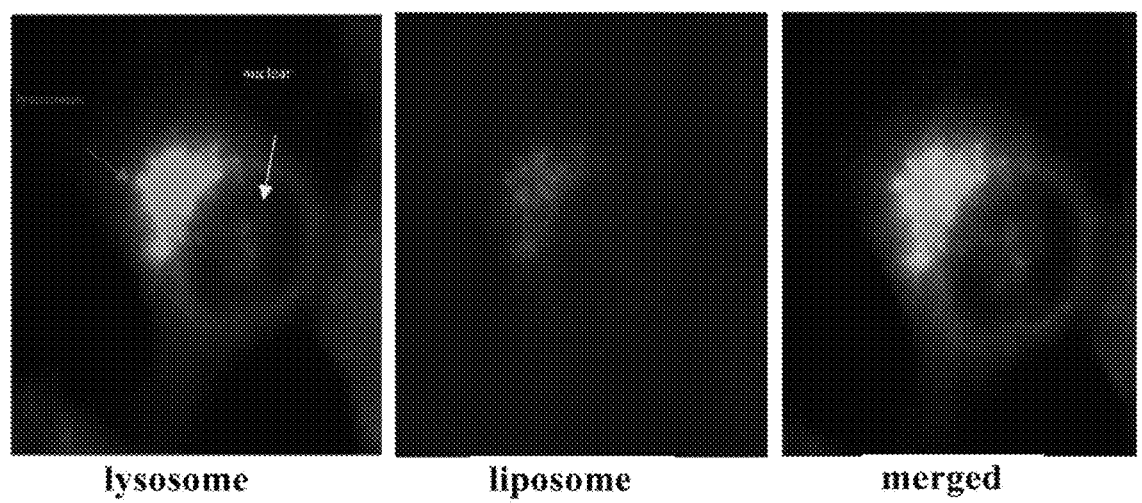
FIG. 14 shows the cellular uptake and exact localization of pH-liposomes.

To confirm the cellular uptake and exact localization of pH-liposomes, we labelled the liposomes with the fluorescent dye rhodamine. The cells were incubated with Rhodamine-labelled liposomes for overnight, and 1 μM lysosensor Green DND-189 (Life Technologies) was used to localize lysosomes. Lysosensor Green DND-189 is non-fluorescent except when inside intracellular acidic compartments such as lysosomes. 1 hour after incubation with lysosensor, the cells were washed and observed with a fluorescent microscope. As shown in FIG. 14, most of the liposomes were colocalized with lysosomes, indicating that lysosomes were the first intracellular site for liposomes when taken up by cells.

Delivery of GGTI in pH-Sensitive Manner and Cell Effects

Figure 15:
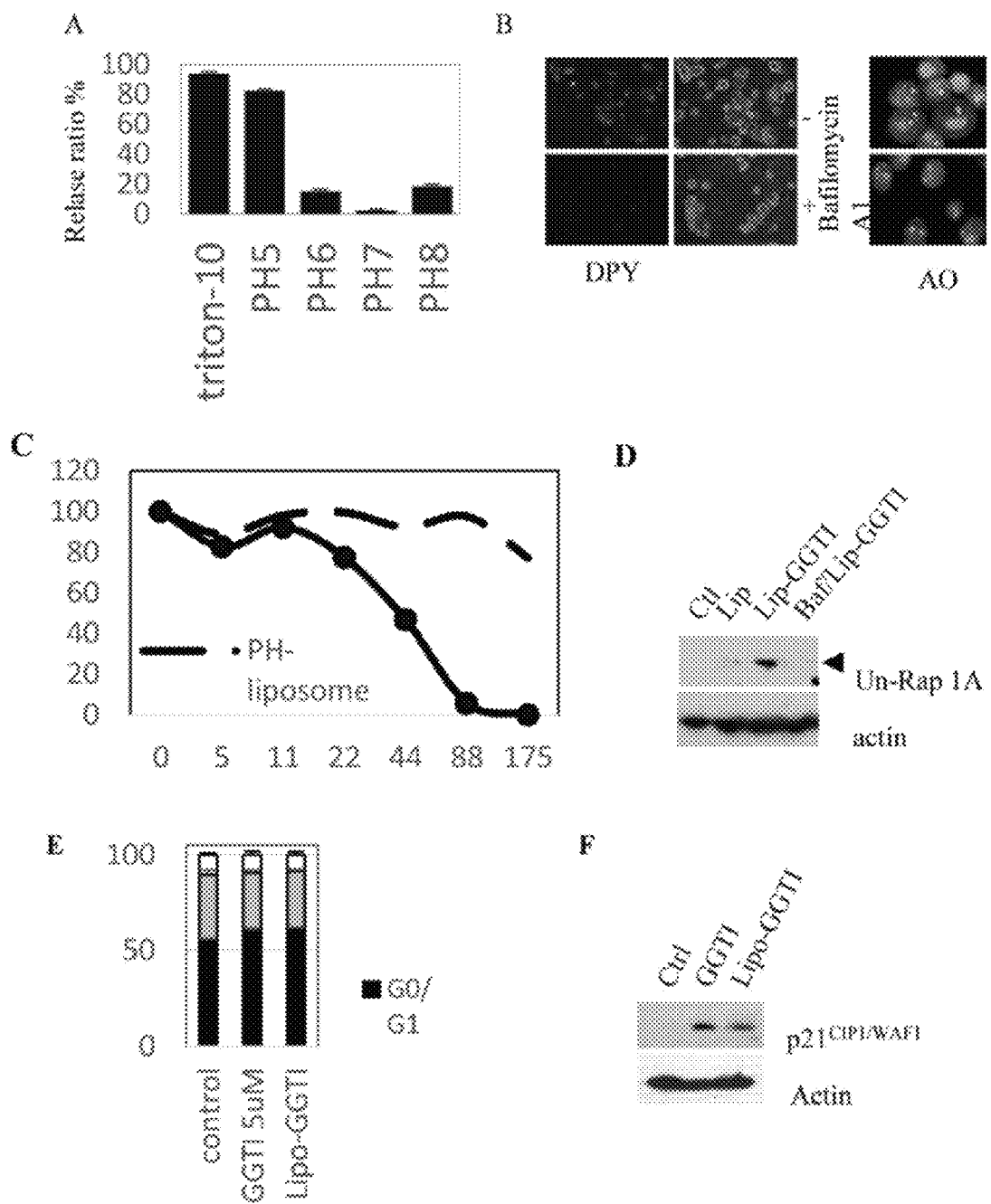
FIG. 15 shows the efficacy of GGTI delivered by pH-sensitive liposomes. (A) release of drug at pH below 6; (B) accumulation of marker in acidic organelles; (C) cell proliferation assay; (D) intracellular protein geranlygenarylation; (E) enrichment of G1 phase cells; (F) accumulation of p21.

As discussed above, nanoparticles of the invention are able to deliver agents loaded therein by the enhanced permeability and retention effect (EPR effect). Since the results above showed that liposomes could effectively deliver chemotherapy drugs such as doxorubicin into cancer cells, the efficacy of GGTI delivered into cells was examined. The inventive pH-liposomes are stable at physiological pH, but become destabilized under acidic conditions, therefore responding to as endosome-lysosome or tumor microenvironment. We examined the pH-sensitive capacity of the polymer-lipidincorporated liposomes using PBS buffer with various pH values ranging from 4.5 to 8. As shown in FIG. 15A, liposomes retained the drugs inside tightly at neutral or basic buffers. Their content release was not observed or negligible at pH 6-8. However, when the pH was below 6, a significant release of GGTI from liposomes was observed, indicating that the pH-sensitive liposomes were efficiently destabilized in the acidic environment. This shows that pH-sensitive liposomes are sensitive, quickly responsive, and efficient for releasing their contents.

The above experiment indicates that liposomes can successfully and effectively deliver drug into cells, and that the pH-sensitive liposome can release the drugs depending on various pH in solution. To test if the intracellular release of cargo molecules is also pH-dependent, a pH-altering compound, Bafilomycin A1, was used to alter pH inside of lysosomes. Bafilomycin A1 (Baf) is a proton inhibitor that can increase lysosomal pH. Cells were treated with 160 nM Baf for 6 hours before DPX dye-loaded pH-sensitive liposomes were added to the cells. To examine the effect of Baf on the de-acidification of lysosomes, acridine orange (AO) staining was performed. AO is a fluorescent weak base that is frequently used as a probe for monitoring the acidification of organelles. In neutral or alkali environments it emits a green fluorescence, but when exposed to acidic compartments, it is ionized and its emission undergoes a redshift. In the untreated cells, red fluorescence was observed inside discrete cytoplasm organelles, indicating that the AO had accumulated in acidic organelles (FIG. 15B). However, the red fluorescence dramatically decreased after 6 hours of Baf treatment, indicating that the Baf had increased the pH of the lysosomes in the MiaPaca-2 cells. pH-liposomes loaded with DPX dye were added to the cells and incubated for an additional 12 hours before examination by fluorescence microscopy. As shown in FIG. 15B, the treatment with Baf completely prevented intracellular release of DPX, demonstrated by the lack of staining, as compared to the bright green fluorescence of the cells unexposed to Baf. This result suggests the intracellular release of dye from pH-liposomes was triggered by the acidity of the lysosomes.

The effect of drug delivery from pH-liposomes was examined with a cell proliferation assay. The pancreatic cancer cell line MiaPaca-2 was treated with unloaded pH-liposomes or GGTI-loaded liposomes for 72 hours. As shown in FIG. 15C, cell proliferation was inhibited starting from a concentration of 40 µg mL-1, which is higher than the concentration of basic liposome-GGTI used to induce cell growth inhibition. This is probably due to incomplete intracellular drug release from pH-liposomes because pH-liposomes escaped from lysosomes would not release the drugs.

To examine if the cell proliferation inhibiting effect was due to the inhibition of GGTase by GGTI that was delivered by liposomes, inhibition of intracellular protein geranylgeranylation, cell cycle effect as well as cellular p21(CIP1/WAF1) accumulation were evaluated. The cells were treated with liposome-GGTI for 3 hours, and proteins were collected from lysated cells for western blot assay. As shown in FIG. 15D, treatment with either GGTI P61-A6 alone or PH-liposome-GGTI led to the appearance of an unprelynated Rap1 band, indicating that liposomes deliver and release GGTI compound inside of cells to function, proving again that liposomes are efficient for intracellular drug delivery. Considering that the pH-liposomes exhibit significant destabilization below pH 6, which corresponds to the pH of the endolysosome interior, the pH-liposomes might cause destabilization or fusion of endolysosomal membrane, resulting in release the drug cargo into cytosol, inhibiting GGTase, therefore blocking Rap 1 prenylation. To examine the pH-sensitivity of pH-liposomes inside of cells, the same experiment was repeated after treating the cells with the pH-altering compound Bafilomycin A1. As shown in FIG. 15D, bafilomycin A1 treatment abolished the effect of pH-liposome-GGTI on Rap1 prenylation. This suggests that the new neutral pH of lysosomes altered by bafilomycin A1 could not destabilize pH-liposomes anymore; therefore, GGTIs were kept inside of liposomes from releasing. Therefore, when taken up by the cells, the acidity of lysosomes is critical for destabilization and/or fusion of pH-liposomes with endolysosome for efficient release and transfer of the contents into cytosol. On the other hand, GGTI P61A6 was known to induce cell cycle arrest at the G1 phase; therefore, the effect on cell cycle of Lipo-GGTI was also examined with Flow cytometry. As shown in FIG. 15E, treatment of MiaPaca-2 cells with either GGTI solution or Lipo-GGTI for 24 h caused enrichment of G1 phase cells, whereas reduced cells in S-phase. Furthermore, the accumulation of G1 phase cells was associated with induction of proteins involved in the regulation of cell cycle, such as p21(CIP1/WAF1), which is a cyclin-dependent kinase inhibitor. As shown in FIG. 15F, both GGTI and Lipo-GGTI treatments induced accumulation of p21(CIP1/WAF1) expression, which is consistent with the cell cycle effect.

4. Combined Use of a Liposomal GGTI and a FTase Inhibitor (FTI)

As noted above, Ras family proteins, such as K-Ras, can be alternatively prenylated by either GGTase or FTase. Blockage of either enzyme individually generally cannot achieve complete inhibition of protein lipid modification, leading to an unsatisfactory clinical outcome for cancer therapy. But blockages of both enzymes at the same time can cause severe toxicity to other normal tissues, because the Ras family is critical for a number of cellular functions. Therefore, preferential and exclusive delivery of GGTI to tumors by using liposomes allows one combine these two types of compounds at the same time for cancer treatment without severe undesired side effects to noncancerous tissues.

Figure 16:
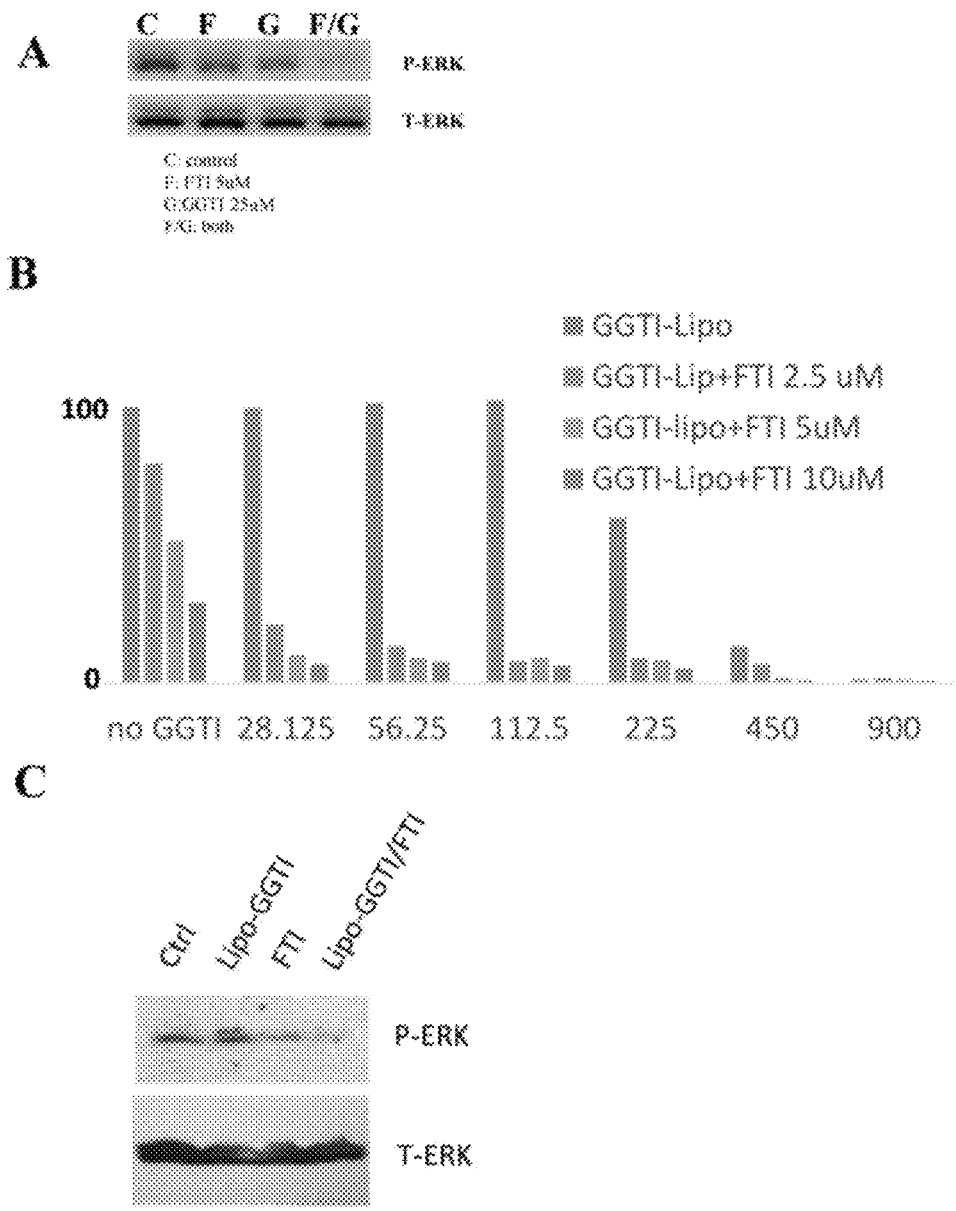
FIG. 16 shows the combined use of GGTI and FTI. (A) Effect of the GGTI/FTI combination without liposomes; (B) Cell proliferation assay; (C) Effect of pH-sensitive liposomes containing GGTI and FTI on the phosphorylation of ERK.

GGTI-loaded pH-liposomes were combined with an FTI compound and cancer cells were treated for 72 hours to examine the combined effect. As shown in FIG. 16B, while liposome-GGTI treatment starts suppressing cell growth at a concentration of 225 ug/ml and higher, adding FTI, even at a concentration as low as 2.5 uM, to liposome-GGTI showed significant suppression of cell proliferation. 28 ug/ml Liposome-GGTI combined with 2.5 uM of FTI suppressed cell proliferation up to approximately 80%, although either single compound at this concentration did not show a significant effect. ERK is a downstream molecule of K-Ras Inhibition of prenylation of K-Ras is reported to block phosphorylation of ERK. Therefore, the effect of phosphorylation of ERK was examined. As shown in FIG. 16C, the combination of FTI and Lipo-GGTI led to complete inhibition of ERK protein expression in cancer cells, which is a critical downstream of k-Ras, while either Lipo-GGTI or FTI alone only partially inhibited its expression.

Discussion

We have described herein our success in encapsulating GGTI into a new type of pH-sensitive liposome. We have encapsulated GGTI into pH-liposomes and demonstrated pH-sensitive release of GGTI. Because the tumor microenvironment is acidic due to a hypoxic effect, this type of liposome is expected to release GGTI once they reach tumor. Thus, these three different liposomal GGTIs provide valuable reagents for cancer therapy using GGTI.

The preparation of liposomal drugs usually requires adjustments of the liposomal composition and also control of the particle size and encapsulation efficiency, which make formulation of liposomal drugs complicated and unstable. One way of overcoming these problems is to use a freeze-dried ready-to-use liposome powder, called Empty Liposomes, which are decomposable SUNBRIGHT DSPE-PG8 liposomes. When a drug solution is mixed with this type of dried liposomes, the drug is simply and easily encapsulated in the liposomes, resulting in a nanoparticle colloidal suspension. Liposomal-GGTI can be reconstituted in normal saline or water, eliminating necessity of using organic solvent which contributes to toxicity. One advantage of basic liposomes is that even drugs such as the anthracyclines and aminoglycosides can be efficiently encapsulated without the need for special technologies such as extrusion. Moreover, with nanoparticles' enhanced permeability and retention effect, liposomal-GGTI prevents undesirable contribution of GGTI in other parts of body, leading to higher intratumor concentration of GGTI, thus better outcome.

Moreover, for cancer targeting, activated functional groups attached to phospholipid, either at the PEG end or the non PEG end, can also be used. For example, transferrin can be conjugated to liposomes. Transferrin (Tf) is an iron-binding glycoprotein made up of single chain peptide. Its receptor's increased expression is also observed in various cancer cells. The receptor is recycled after uptake of Tf into the cell, and there is no fusion with lysosome after internalization. Therefore, Transferrin as a target ligand for cancer cells is useful and efficacious. Previous studies reported that liposomes with Tf conjugated to an end of PEG-attached phospholipid are significantly more easily taken up by cancer cells than PEG liposomes without Tf. However, after having been taken up by the cells, it is not clear how the therapeutic agents in a liposome are actually released. Therefore, the intracellular drug release is not controllable.

Figure 13:
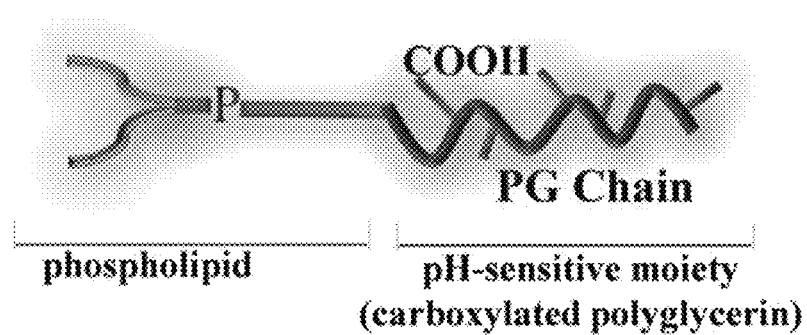
FIG. 13 is a cartoon of a pH-sensitive liposome.

To be able to control drug release inside of the cells, we developed a type of pH-sensitive liposome. See FIG. 13. These liposomes are stable at physiological pH, but become destabilized and fusogenic under acidic conditions, such as endosome-lysosome or tumor microenvironment, effectively releasing encapsulated drugs under the acid conditions. Utilizing these new types of liposomes, we have achieved a liposomal modified GGTI compound with efficient loading and releasing capacity, and tumor-targeting delivery, as well as pH-responsive controllable intracellular drug release.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications, cited above and in the figures, are hereby incorporated in their entirety by reference, particularly with reference to the subject matter for which they are cited.

We claim:

1. A liposome, which is

A basic liposome, or a transferrin-conjugated liposome, or a pH-sensitive liposome, wherein the liposome encapsulates a compound having the formula

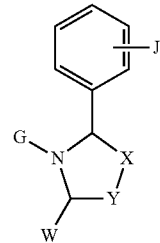

wherein J is hydrogen or is 1-2 substituents independently selected from the group consisting of halogen, C1-C3 alkyl, OR', SR', and NR'2, where R' is alkyl, wherein G is

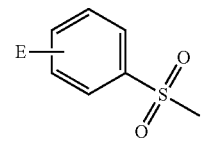

wherein E is hydrogen or is 1-2 substituents selected from the group consisting of halogen, C1-C3 alkyl, OR', SR', and NR'2, where R' is alkyl, wherein W is selected from the group consisting of hydrogen, cyclic, linear, or branched alkyl of from 2 to 8 carbons, unsubstituted phenyl. and phenyl substituted with C1-C3 alkyl, halogen, OR', SR', and NR'2, where R' is alkyl, wherein

is selected from the group consisting of

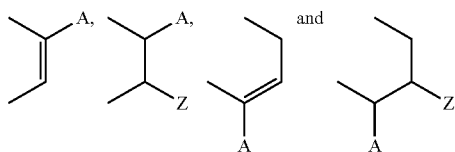

wherein A is selected from the group consisting of:

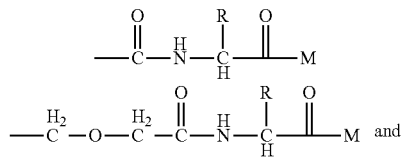

-continued

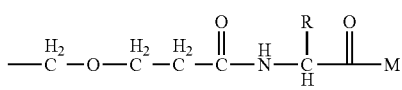

wherein M is selected from the group consisting of OH, OR", NH2, NHOH, NHOR", wherein R" is methyl or ethyl, or any other group that has a polar metal binder wherein R corresponds to an alpha-substituent of natural or non-natural alpha-amino acid;

wherein Z is S—U: and wherein U is selected from the group consisting of alkyl having 10 or fewer carbons, phenyl, optionally substituted with halogen or OR", wherein R" is methyl or ethyl, and (CH2)n-COOR4, wherein n=1-4 and R4 is a linear or branched alkyl having four or fewer carbons;

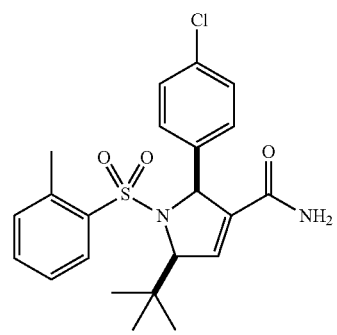 [SMILES: Cc1ccccc1S(=O)(=O)N1[C@@H](c2ccc(Cl)cc2)C(C(N)=O)=C[C@H]1C(C)(C)C]

or the compound P61-A7.

2. The liposome of claim 1, wherein A is

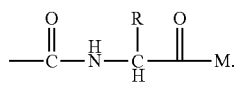

3. The liposome of claim 1, wherein A is

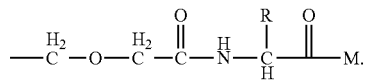

4. The liposome of claim 1, wherein A is

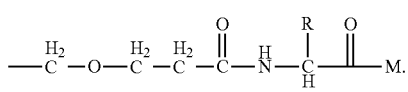

5. The liposome of claim 1, wherein M is OEt, OMe, Ot-Bu, OH, NH2, NHOH, NHOMe, or any other groups that have a polar metal binder.

6. The liposome of claim 1, wherein the compound is selected from the group consisting of

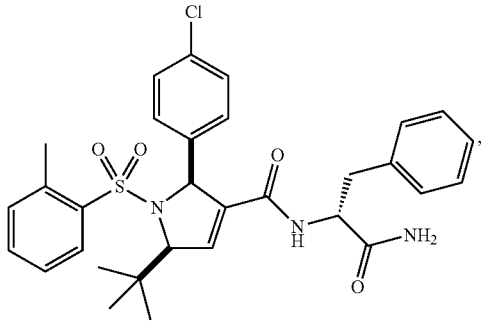

P61-A6

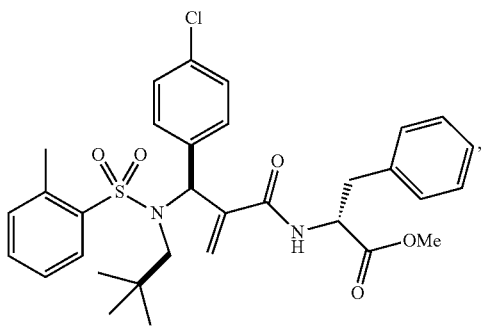

P61-A5

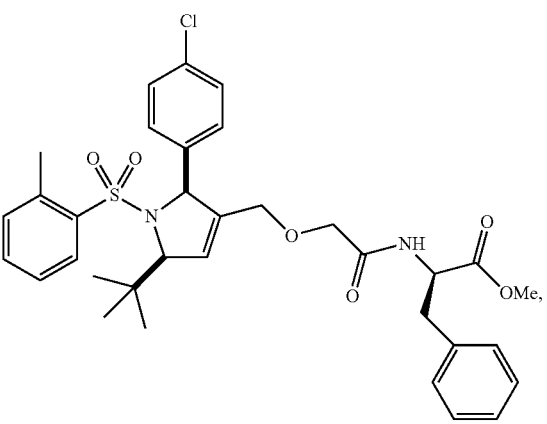

P61-B4

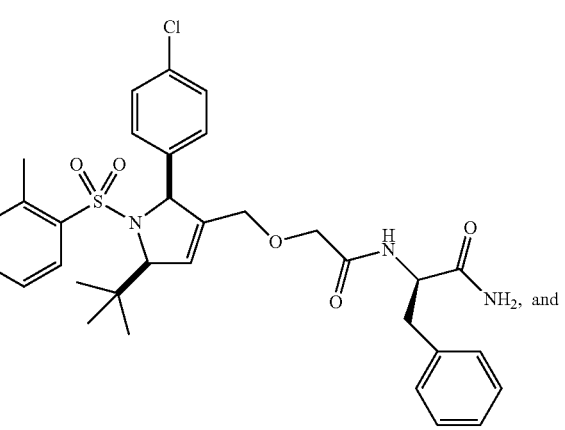

P61-B6, and

-continued

P61-E7

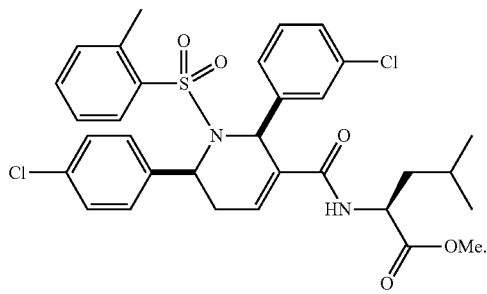

7. The liposome of claim 1, wherein G is

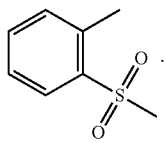

8. The liposome of claim 1, which inhibits the activity of a protein prenyltransferase.

9. The liposome of claim 1, which inhibits the activity of a RabGGTase.

10. The liposome of claim 1, which inhibits the activity of GGTase I.

11. The liposdome of claim 1, which inhibits the activity of GGTase I and RabGGTase.

12. A method comprising administering the liposome of claim 1 to a cell in an amount sufficient to inhibit the activity of GGTase I and/or RabGGTase.

13. The method of claim 12, wherein the liposome is administered at a microgram/ml concentration.

14. A method comprising administering a liposome of claim 1 in an amount sufficient to inhibit the growth of a cancer cell or to reduce the size of a tumor of cancer cells.

15. The method of claim 14, wherein the cancer cell comprises GGTase I and/or RabGGTase modified proteins.

16. A method comprising administering to a subject in need of treatment for a cancer the liposome of claim 1 in an amount sufficient to inhibit the activity of a protein prenyltransferase.

17. The method of claim 16, wherein the protein prenyltransferase is GGTase I, RabGGTase, or both.

18. The method of claim 16, wherein the cancer cell comprises GGTase I and/or RabGGTase modified proteins.

19. The method of claim 16, further comprising administering to the subject an inhibitor of farnesyltransferase (FT), wherein the liposome and the FT inhibitor together are in an amount sufficient to inhibit the growth of a cancer cell or to reduce the size of a cancerous tumor.

20. A method comprising measuring the GGTase I and/or RabGGTase inhibiting activity of a liposome of claim 1.

21. A method of preparing a liposome of claim 1, comprising introducing a solution comprising the compound into a vessel containing a preformed liposome, collecting the loaded liposome by centrifugation, and resuspending the collected liposome in a suitable buffer.

22. A kit comprising a liposome of claim 1, in a container.

23. A method of delivering the liposome of claim 1 to a patient in need thereof, the method comprising:
  registering in a computer readable storage medium the identity of a physician permitted to prescribe the liposome;
  providing the patient with counseling information concerning a risk attendant to the liposome;
  obtaining informed consent of the patient to receive the liposome despite the risk;
  registering the patient in the computer readable medium after obtaining the informed consent; and
  permitting the patient access to the liposome.

24. The liposome of claim 1, which is a pH-sensitive liposome, wherein the liposome comprises a ratio of the two lipids POPC and DSPE-PG8MG of about 85/15, and wherein the liposome is sensitive to a pH of about 6.0 or lower.

25. A compound or salt thereof having the formula

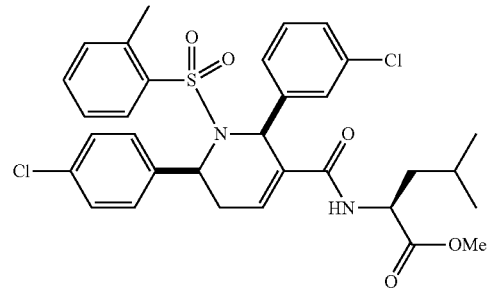

or a pharmaceutical composition thereof which also comprises a pharmaceutically acceptable carrier.

* * * * *